US006793924B2

(12) United States Patent
Lederman et al.

(10) Patent No.: US 6,793,924 B2
(45) Date of Patent: Sep. 21, 2004

(54) PROTEIN RECOGNIZED BY AN ANTIBODY THAT SPECIFICALLY BINDS AN EPITOPE THAT IS SPECIFICALLY BOUND BY MONOCLONAL ANTIBODY 5C8.

(75) Inventors: Seth Lederman, New York, NY (US); Leonard Chess, Scarsdale, NY (US); Michael J. Yellin, Riverdale, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 10/183,903

(22) Filed: Jun. 25, 2002

(65) Prior Publication Data

US 2003/0077280 A1 Apr. 24, 2003

Related U.S. Application Data

(60) Continuation of application No. 09/291,667, filed on Apr. 14, 1999, now Pat. No. 6,455,044, which is a continuation of application No. 08/484,137, filed on Jun. 7, 1995, now Pat. No. 6,451,310, which is a division of application No. 07/792,728, filed on Nov. 15, 1991, now Pat. No. 5,474,771.

(51) Int. Cl.[7] ...................... A61K 38/17; C07K 14/705; C07K 16/28

(52) U.S. Cl. ...................... 424/184.1; 514/2; 514/8; 514/885; 530/350; 530/387.1; 530/388.2; 530/388.22; 530/388.7; 530/388.73; 530/388.75

(58) Field of Search ...................... 424/184.1; 514/2; 530/350, 388.22, 388.75; 435/326, 343.1

(56) References Cited

U.S. PATENT DOCUMENTS

| 5,102,909 A | 4/1992 | Veltri et al. |
|---|---|---|
| 5,340,829 A | 8/1994 | Clark et al. |
| 5,474,771 A | * 12/1995 | Lederman et al. |
| 5,683,693 A | 11/1997 | Noelle et al. |
| 5,747,037 A | 5/1998 | Noelle et al. |
| 5,833,987 A | 11/1998 | Noelle et al. |
| 5,961,974 A | * 10/1999 | Armitage et al. |
| 6,455,044 B1 | * 9/2002 | Lederman et al. |

FOREIGN PATENT DOCUMENTS

| EP | 0555880 | 8/1993 |
|---|---|---|
| WO | WO 9506480 | 3/1995 |
| WO | WO 9623071 | 8/1996 |
| WO | WO 9830240 | 7/1998 |
| WO | WO 98302417 | 7/1998 |

OTHER PUBLICATIONS

Skolnick et al. Trends in Biotechnology 18:34–39 (2000).*
Bost et al. Immunol Invest. 17:577–586 (1988).*
Li et al. PNAS 77:3211–3214 (1980).*
Akdis et al. (1997) Eur. J. Immunol. 27:2351–2357.
Bartlett, W.C., et al. (1990). J. Immunol. 145: 3956–3962.
Biacone et al. (1999) Int. J. Mol. Med. 3(4):343–53.
Biogen Press Release 10.21.99.
Biogen Press Release 11.2.99.
Callard et al. (1993) Imm.Today 14:559–564.
Christadoss, P. and Dauphinee, M.J. (1986) J. Immunol.136:2437–2440.
Clark, E.A. and Ledbetter, J.A. (1986) Proc. Natl. Acad. Sci.USA 83: 4494–4498.
Clark E. (1990) Tiss. Ags.36(1):33–36.
Cosimi A.B. et al (1981) Transplant Proc 13:499–503.
Durie et al. (1994) J. Clin. Invest. 94:1333–38.
Edgington et al. (1993) Biotech. 11:998–1000.
Elkayam, O., M. Yaron and D. Caspi, (1999) Semin. Arthritis Rheum. 28:392.
Freeman, G. J., et al.(1991). J. Exp. Med. 174:625–631.
Gascan H. et al. (1991) J. Immunol 147:8–13.
Goldberg D. et al. (1991) J. Autoimmun. 4:617–630.
Gordon J. et al. (1988) J. Immunol. 140:1425–1430.
Graf D. et al. (1992) Eur. J. Imm..22(12):3191–94.
Hafler D.A. (1988) J. Immunol 141:131–138.
Haynes M. K. et al. (1987) Diabetes 36:877–881.
Horneff G. et al. (1991) Arthritis & Rheum. 34:129–140.
International Preliminary Examination Report for PCT/US97/23482, 2.11.99.
International Preliminary Examination Report for PCT/US97/00573, 4.7.99.
Jain, Jul. 1994 Sci. Am. pp 58–65.
Jenkins M.K. et al. (1987) J. Exp. Med. 165:302–319.
Junghans R.P. (1990) Cancer Res. 50:1495–1502.
Kennedy M.K .(1987) J. Neuroimmunol. 16:345–364.
Koike T. (1987) Diabetes 36:539–541.
Kover K.L. et al (2000) Diabetes 49(10):1666–70.
Kung P.C. et al. (1979) Sci. 206:347–349.
Kung P.C. et al. (1980) Vox. Sang. 39:121–127.
Lassman H. et al. (1998) J. Neuroimmunol. 86:213.
Laverma et al. (1997) Biodrugs 8:96–106.
Lederman S. et al. (1994) Res. in Imm. 145(3):215–221.
Lenz et al. (1993) J. Clin. Invest. 92:2587–2596.
Ling N.R. (1987) A.J. Michaels ed p302–35.
Linsley P.S. et al. (1991) J. Exp. Med. 174:561–569.
Madec A.M. et al. (1996) J. Immunol. 156:3541–3549.

(List continued on next page.)

Primary Examiner—Phillip Gambel
(74) Attorney, Agent, or Firm—John P. White; Cooper & Dunham LLP

(57) ABSTRACT

This invention provides a protein free of cell membranes and other cellular components, said protein being specifically recognized by an antibody that specifically binds an epitope that is specifically bound by monoclonal antibody 5c8 produced by the hybridoma having ATCC Accession No. HB 10916. This invention further provides a protein that is a fragment of a protein specifically recognized by monoclonal antibody 5c8 produced by the hybridoma having ATCC Accession No. HB 10916, wherein said fragment is free of cell membranes and other cellular components and comprises an epitope that is specifically bound by monoclonal antibody 5c8 produced by the hybridoma having ATCC Accession No. HB 10916. This invention also provides a protein free of cell membranes and other cellular components, said protein consisting essentially of an epitope that is specifically bound by monoclonal antibody 5c8 produced by the hybridoma having ATCC Accession No. HB 10916.

6 Claims, 13 Drawing Sheets

OTHER PUBLICATIONS

Mandik–Nayak L. (2000) *J. Imm.* 164(3):1161–68.
Marshall L. S. et al. (1990) *Res. Immunol.* 141:412–417.
McCormick A.L. (1999) *Cell Imm.* 195(2):157–161.
Noelle R.J. et al. (1996) *Immunity* 4:415–19.
Noelle R. (1990) *Imm.Today* 11(10):361–68.
Paul (Ed) *Fund. Imm.*, Raven Press p459–460.
Paul (Ed) *Fund. Imm.*, Raven Press p242.
Paulie et al. (1985) *Cancer Immunol. Immunother.* 20:23–28.
Pisetsky D.S. (1985) in Pincus S.H. et al eds. p171–76.
Potocnik A.J. et al. (1990) *Scand. J. Immol.* 31:213–224.
Ranges G.E et al. (1985) *J. Exp. Med.* 162:1105–1110.
Reeman G.J. et al. (1991) *J. Exp. Med.* 174:625–31.
Reinherz E.L. et al. (1979) *J. Exp. Med.*150:1472–1482.
Reiter C. et al. (1991) *Arthritis & Rheum.* 34:525–36.
Rousset et al. (1991) *J. Exp. Med.* 173:705.
Satoh J. et al. (1988) *J. Neuroimmunol.*18:105–116.
Schwarz R.H. et al. (1990) *Sci.* 248:1349–1356.
Seung K. et al. (2000) *Blood* 95(6):2175–82.
Shizuru J.A. et al. (1988) *Sci.* 240659–662.
Smiley, J.D. and S.E. Moore, Jr., (1988) *Am. J. Med. Sci.* 295:478.
Snow E. C . et al. (1989) *Fed. Am. Soc. for Exp. Bio. 73$^{rd}$ meeting Abs No.* 4267.
Sriram S. et al. (1986) *J. Immunol.* 136:4464–69.
Stuber et al. (1996) *J. Exp. Med.* 183:693–698.
Stull S.J. at al. (1988) *Cell Immunol.* 117:188–98.
Traugott U. (1983) *Science* 219:308–310.
Traugott U. (1983) *J. Neuroimmunol.* 4:201–21.
Valent P. et al. (1990) *Int. Arch. Allergy. Appl. Immunol.*91:198–203.

van Seventer G.A. et al. (1990)*J. Immunol.* 144:4579–4586.
Waldmann H. et al. (1989) *Ann. Rev. Immunol.* 7:407–444.
Waldor M.K. et al (1985) *Sci.* 227:415–17.
Williams I.R. et al. (1990) *J. Immunol.* 145:85–93.
WO 9830240, Biogen, written op.10.12.98.
WO 9830241, Biogen, written op.10.12.98.
WO 9830241, Biogen, reply to written op.01.08.99.
WO 9830240, Biogen, reply to written op.01.08.99.
Wofsy, D., et al. (1985). *J. Immunol.*134:852–857.
Wofsy, D. and Seaman, W.E., (1985). (S.H. Pincus, et al. eds.), pp. 187–195.
Wofsy, D. and Seaman, W.E. (1985). *J. Exp.Med.* 161:378–391.
Wofsy, D. and Seaman, W.E. (1987). *J. Immunol.* 138:3247–3253.
Wofsy, D. (1986). *J. Immunol.* 136:4554–4560.
Wofsy, D. and Carteron, N.L. (1990). *Semin. Immunol.* 2:419–425.
Young, L.S., et al. (1989) *Int. J. Cancer* 43:786–794.
Strom T.B. et al. 1989, "Toward More Selective Therapies to Block Undesired Immune Responses", *Kidney International* 35(4):1026–1033.
Yellin M.J. et al. 1991, "A Human CD4 negative T–Cell Leukemia Cell Subclone with Contact–Dependent Helper Function", *Journal of Immunology* 147(10):3389–3395.
Lederman S. et al. 1992, "Anti–CD40 Monoclonal Antibody Blocks the Contact Dependent T Helper Signal Medicated by 5c8 Antigen", *Clinical Research* 40(2):154A.

* cited by examiner

FIGURE 1A
CD4+
FIGURE 1B
CD4-
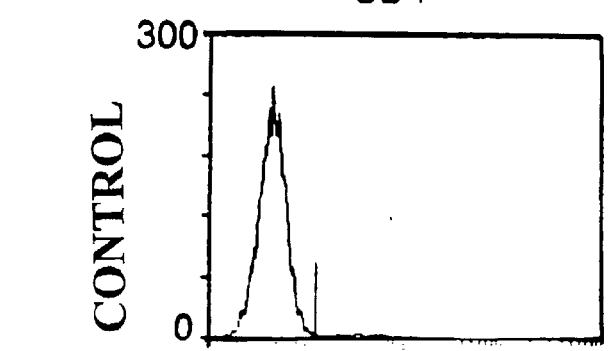
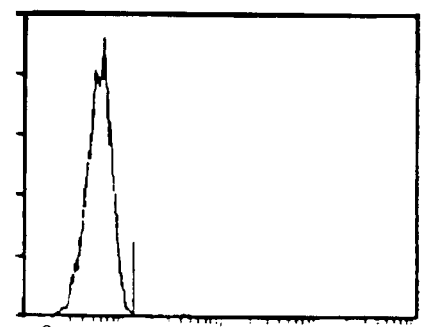
FIGURE 1C
FIGURE 1D
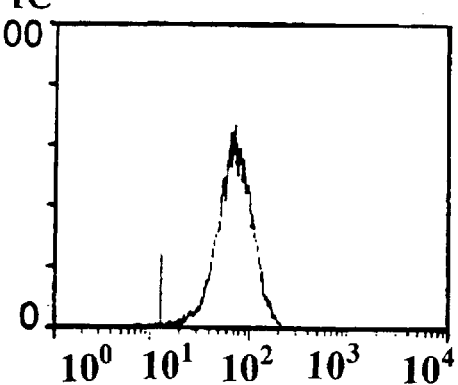
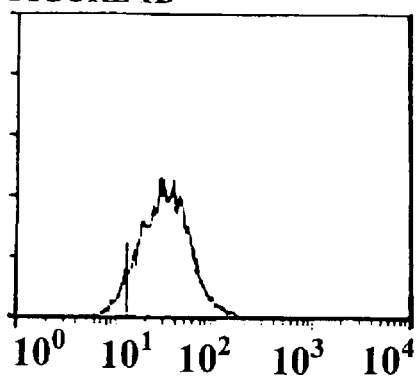
FIGURE 1E
FIGURE 1F
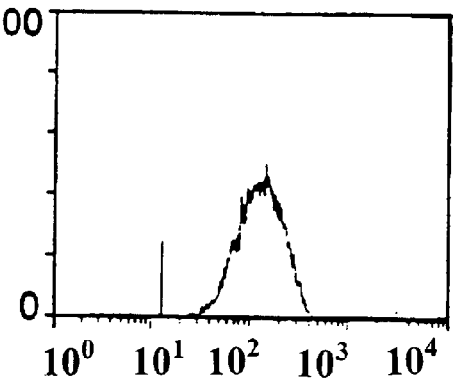
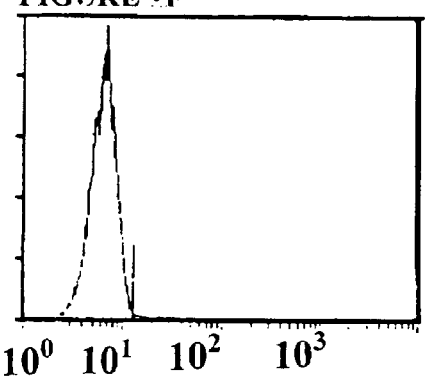
FIGURE 1G
FIGURE 1H
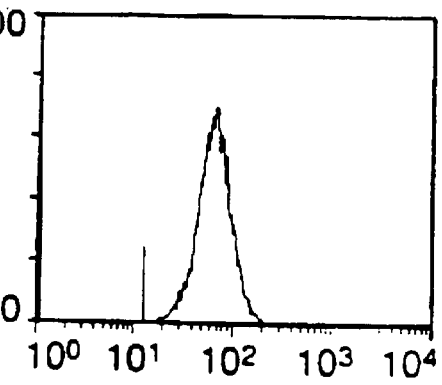
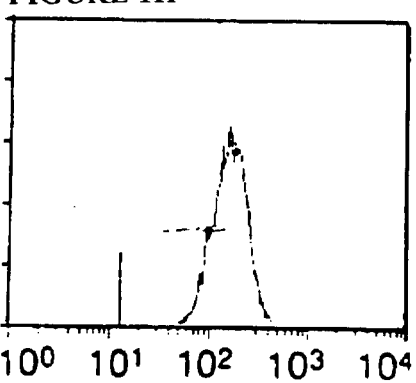

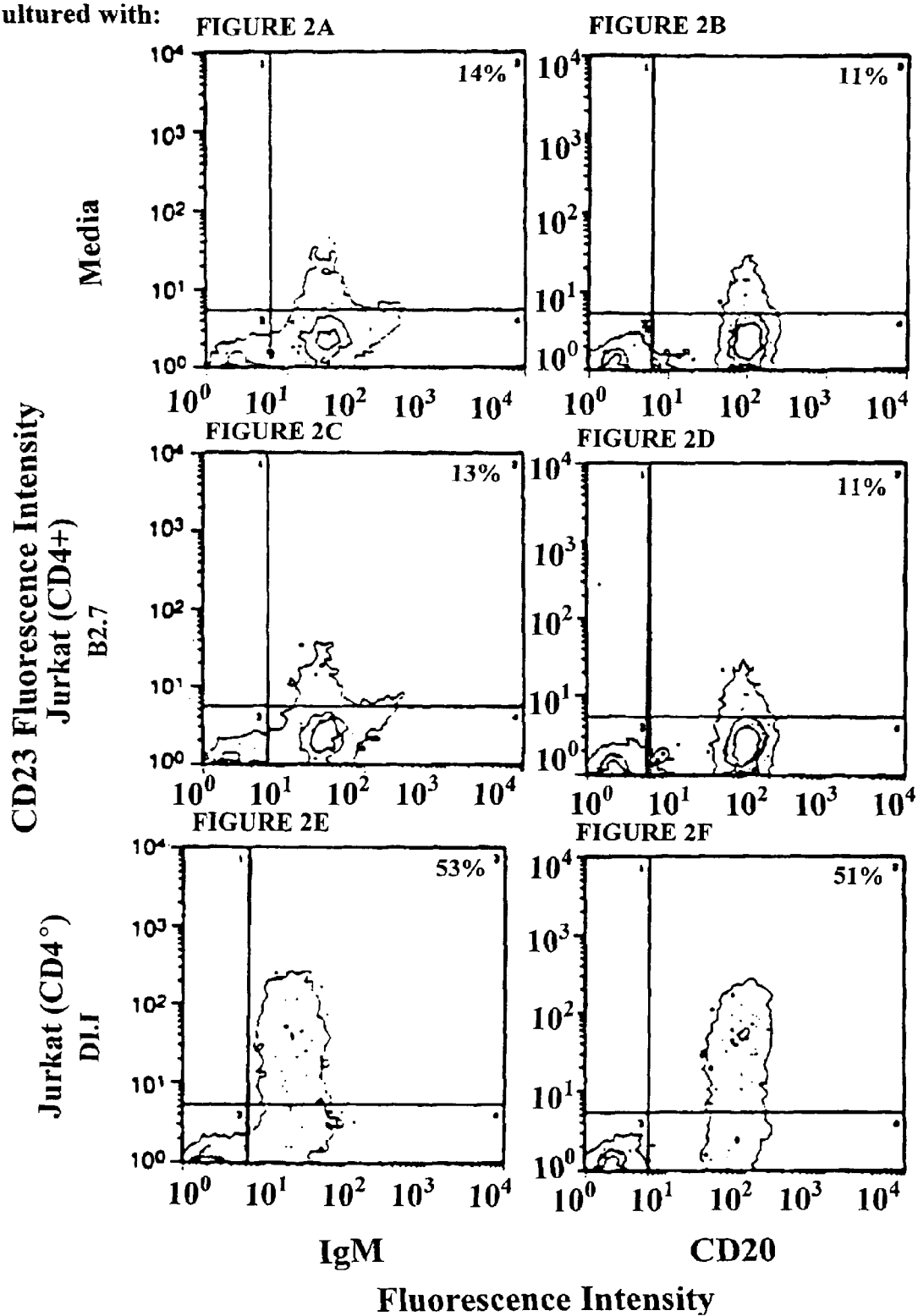

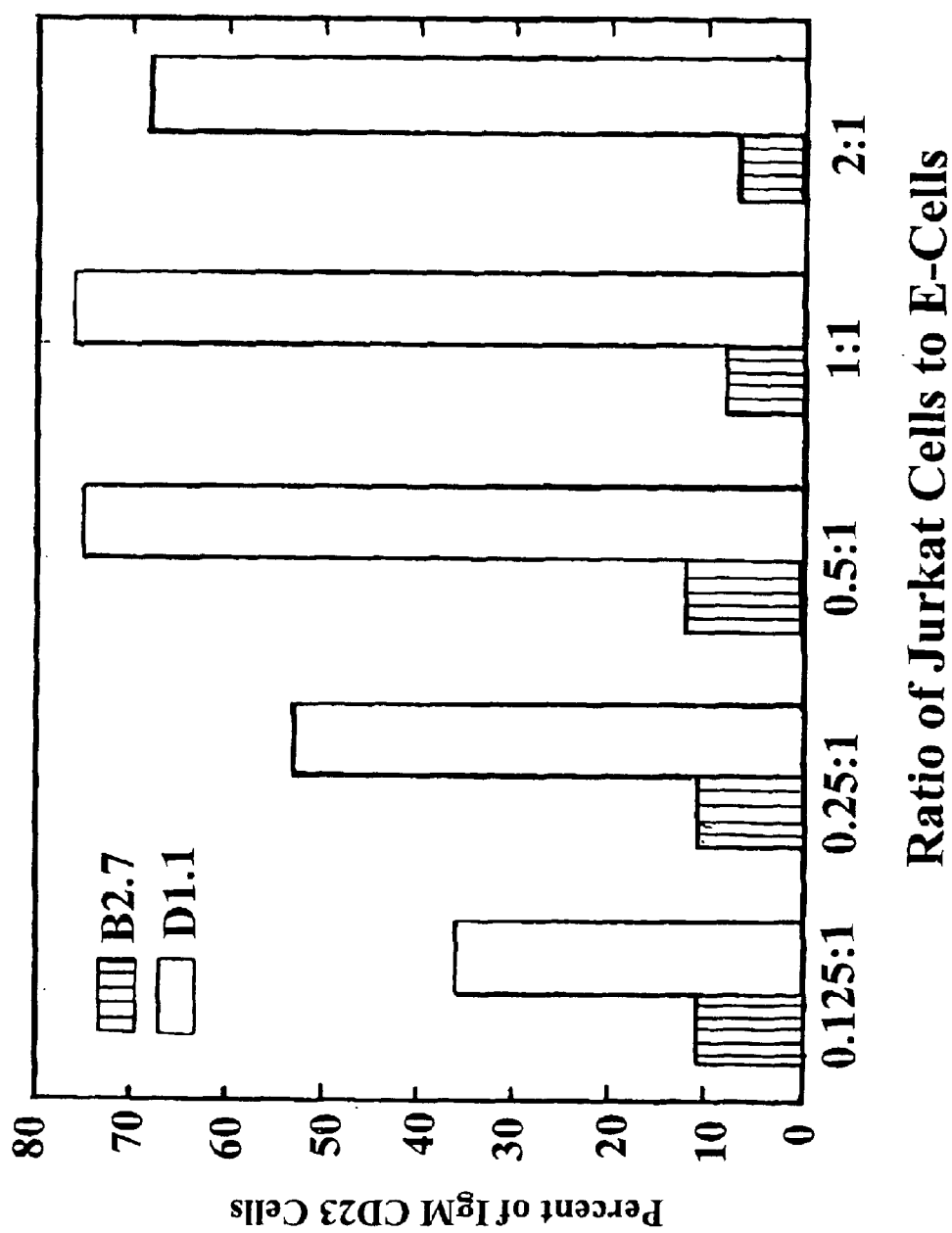
FIGURE 3A
FIGURE 3B

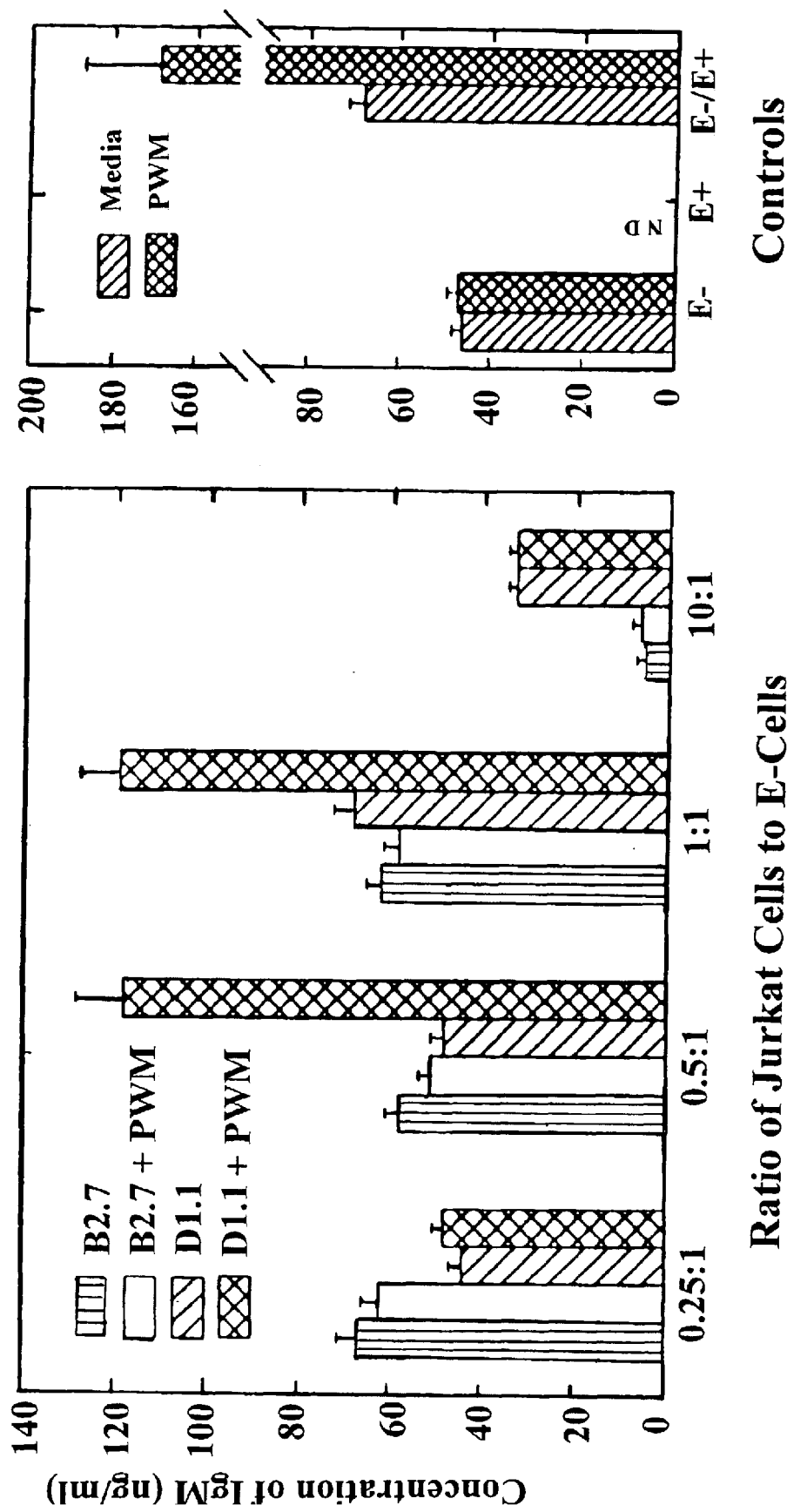

B cells cultured with:

IgG mean channel fluorescence

40

Jurkat B2.7

34

Jurkat D1.1

44 rIL2

100 rIL4

41 rIL4 + anti-IL4 anti-IgM Fluorescence anti-CD23 Fluorescence

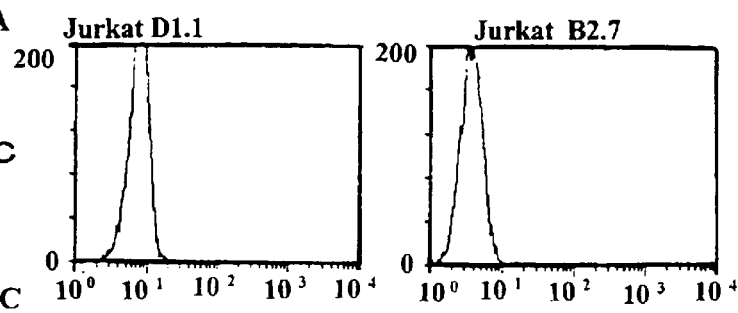
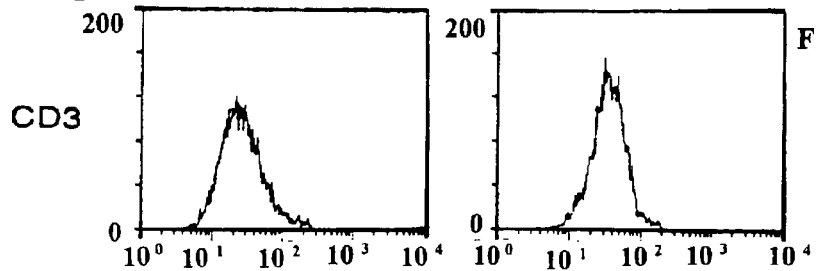
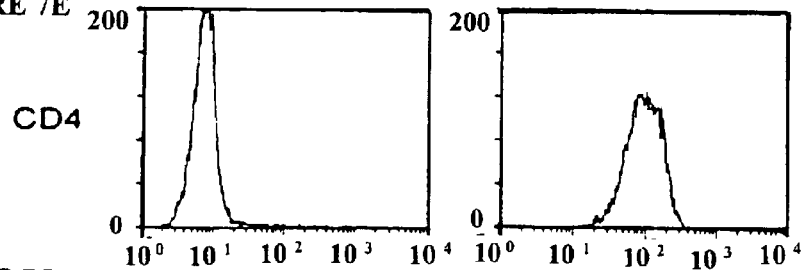
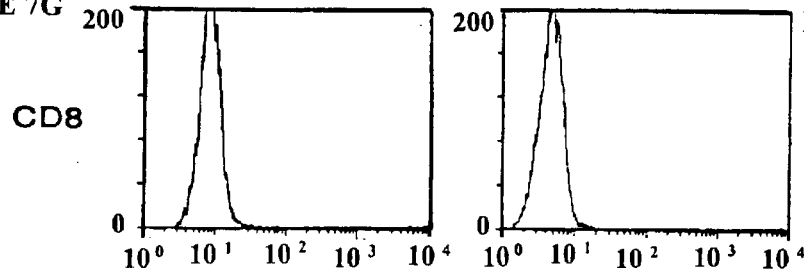
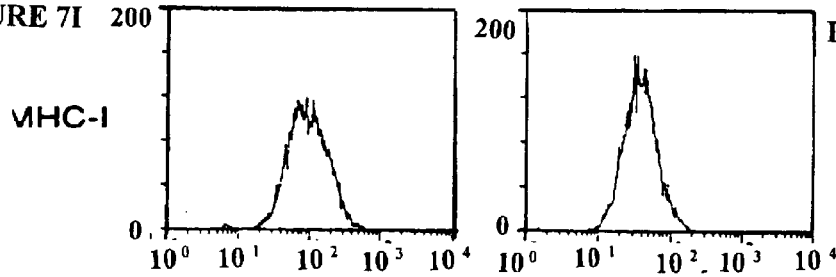
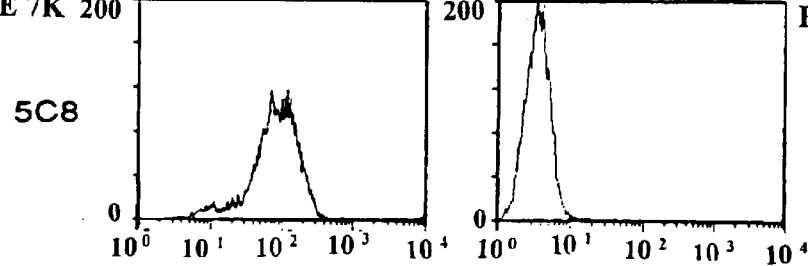

B cells cultured with:

anti-CD23 Fluorescence anti-IgM-Fluorescence

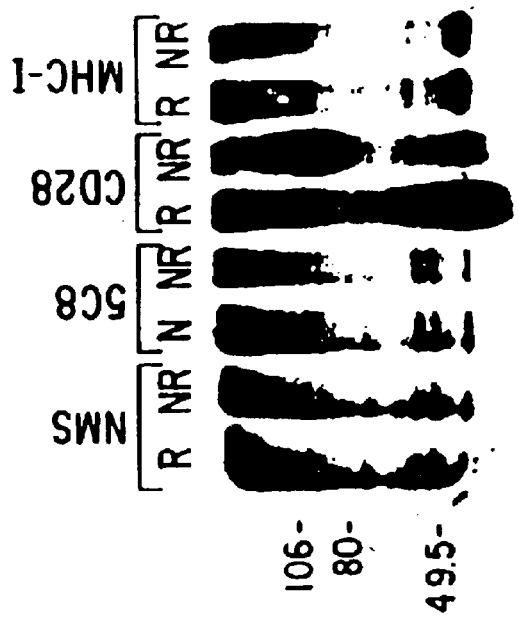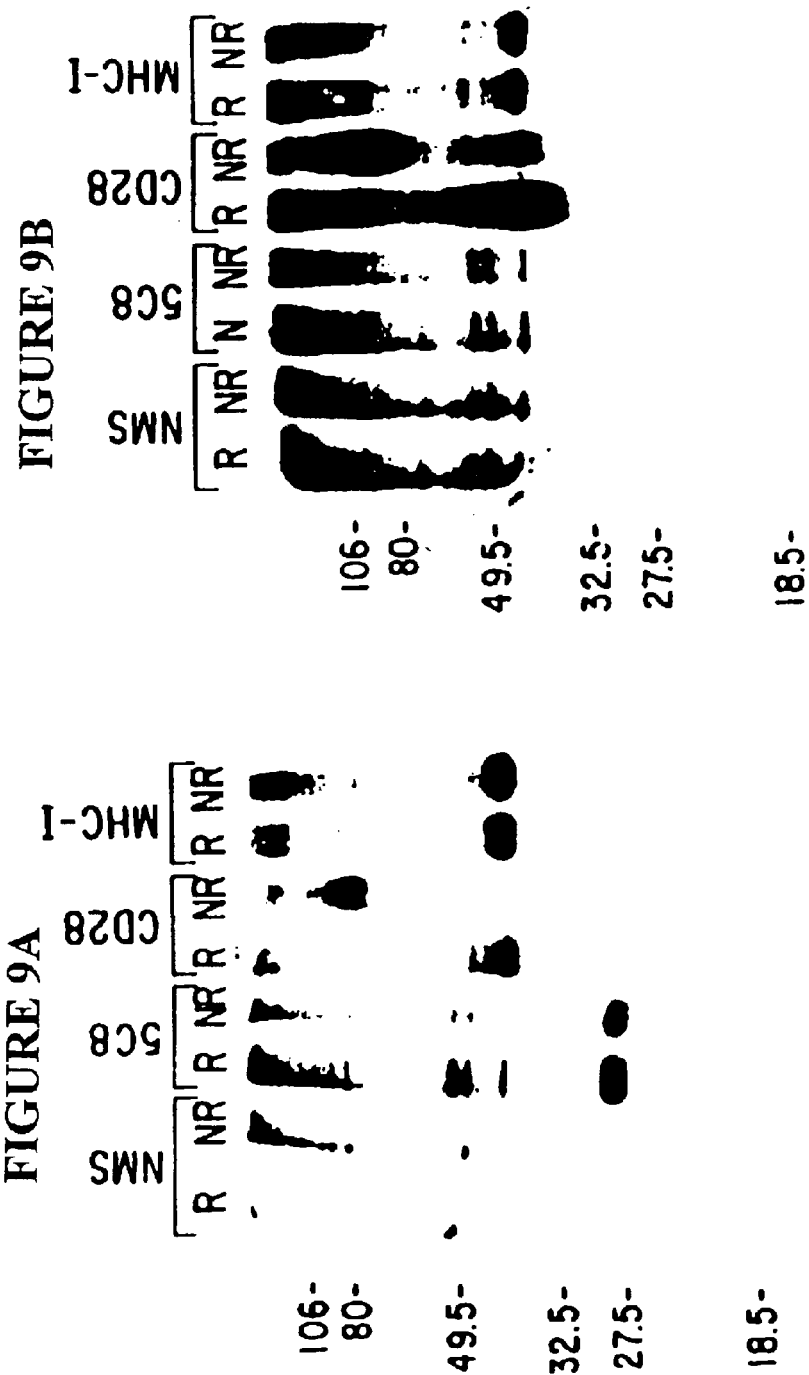
FIGURE 9A  FIGURE 9B

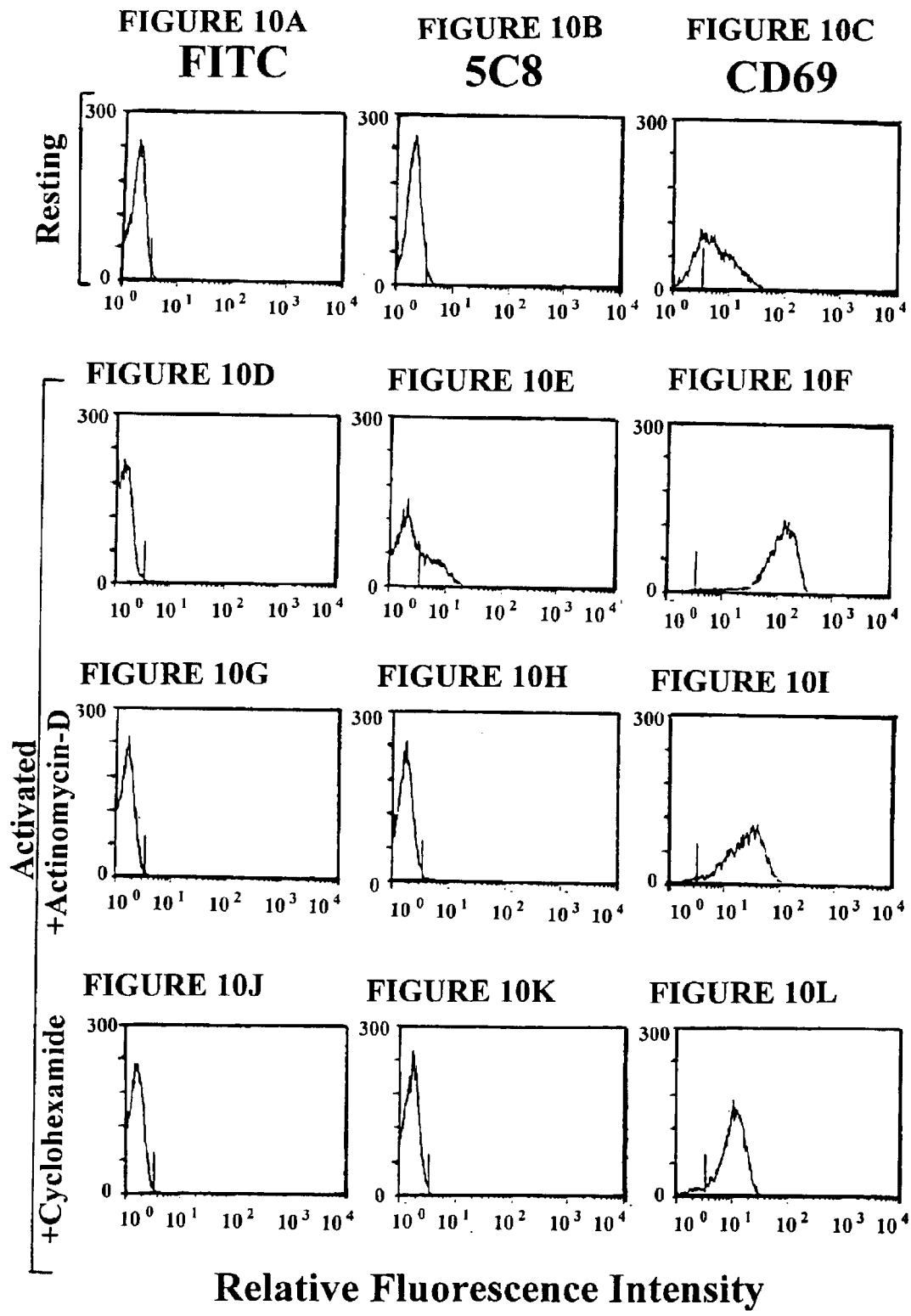

Mean Fluorescence

PROTEIN RECOGNIZED BY AN ANTIBODY THAT SPECIFICALLY BINDS AN EPITOPE THAT IS SPECIFICALLY BOUND BY MONOCLONAL ANTIBODY 5C8.

This application is a continuation of U.S. Ser. No. 09/291,667, filed Apr. 14, 1999, now U.S. Pat. No. 6,455,044 B1, which is a continuation of U.S. Ser. No. 08/484,137, filed Jun. 7, 1995; now U.S. Pat. No. 6,451,310 B1, which is a divisional of U.S. Ser. No. 07/792,728, filed Nov. 15, 1991, now U.S. Pat. No. 5,474,771, the contents of each of which are hereby incorporated by reference into the present application.

The invention described herein was made in the course of work under grant Nos. PO1-AI-26886, RO-1-AI-14969 and Immunology Training Grant AI-07132 from the National Institutes of Health. The United States government therefore has certain rights in this invention.

BACKGROUND OF THE INVENTION

Throughout this application, various publications are referenced by Arabic numerals within parenthesis. Full citations for these publications may be found at the end of the specification, immediately preceding the claims. The disclosures of these publications are hereby incorporated by reference into this application in order to more full describe the state of the art as to one skilled therein as of the date of the invention described and claimed herein.

In a contact-dependent process termed "T cell helper function," $CD4^+$ T lymphocytes direct the activation and differentiation of B lymphocytes and thereby regulate the humoral immune response by modulating the specificity, secretion and isotype-encoded functions of antibody molecules (1–8). The T cell surface molecules that mediate the contact-dependent elements of T cell helper function are not yet fully known (9).

The process by which T cells help B cells to differentiate has been divided into two distinct phases: the inductive and effector phases (10,11). In the inductive phase, resting T cells contact antigen-primed B cells and this association allows clonotypic T cell receptor (TCR)-CD4 complexes to interact with Ia/Ag complexes on B cells (5, 12–19). TCR/CD4 recognition of Ia/Ag results in the formation of stable T-B cognate pairs and bidirectional T and B cell activation (20–26). In the effector phase, activated T cells drive B cell differentiation by secreting lymphokines (27–30) and by contact-dependent stimuli (24,31–38), both of which are required for T cells to drive small, resting B cells to terminally differentiate into Ig secreting cells (31, 39–42).

Although the inductive phase of T cell help is Ag-dependent and MHC-restricted (5, 12–18, 40), the effector phase of T cell helper function can be Ag-independent and MHC-nonrestricted (31, 34, 36, 40, 43–50). An additional contrasting feature is that the inductive phase of T cell help often requires CD4 molecules and is inhibited by anti-CD4 mAb (19), whereas helper effector function does not require CD4 molecules (51) and is not inhibited by anti-CD4 mAbs (33, 34, 36, 49). The nonspecific helper effector function is believed to be focused on specific B cell targets by the localized nature of the T-B cell interactions with antigen specific, cognate pairs (25, 26, 52).

Although terminal B cell differentiation requires both contact- and lymphokine-mediated stimuli from T cells, intermediate stages of B cell differentiation can be induced by activated T cell surfaces in the absence of secreted factors (32, 33, 53–56). These intermediate effects on B cells include induction of surface CD23 expression (32, 35, 57), enzymes associated with cell cycle progression (37) and responsiveness to lymphokines (24, 37, 49, 54–56). Although the activation-induced T cell surface molecules that direct B cell activation have not been previously identified, functional studies have characterized some features of their induction and biochemistry. First, T cells acquire the ability to stimulate B cells 4–8 h following activation (38, 49). Second, the B cell stimulatory activity associated with the surfaces of activated T cells is preserved on paraformaldehyde fixed cells (24, 32, 37, 49, 56) and on purified membrane fragments (33, 53–55). Third, the B cell stimulatory activity is sensitive to protease treatment (24, 53, 54). Fourth, the process of acquiring these surface active structures following T cell activation is inhibited by cyclohexamide (49, 54). Although these studies strongly suggest the existence of activation-induced T cell surface proteins that deliver contact dependent stimuli to B cells, the molecular identities of such structures have not previously been described.

SUMMARY OF THE INVENTION

This invention provides a monoclonal antibody which specifically recognizes and forms a complex with T-B cell activating molecule (T-BAM) (now also known as CD40 ligand) a protein located on the surface of activated T cells and thereby inhibits T cell activation of B cells. This invention also provides the monoclonal antibody 5c8 (ATCC Accession No. HB 10916).

This invention provides a human $CD4^-$ T cell leukemia cell line designated D1.1 (ATCC Accession No. CRL 10915) capable of constitutively providing contact-dependent helper function to B cells. This invention also provides an isolated protein from the surface of activated T cells, wherein the protein is necessary for T cell activation of B cells. This invention further provides an isolated, soluble protein from the surface of activated T cells, wherein the protein is necessary for T cell activation of B cells.

Monoclonal antibody 5c8 and a human CD4− T-cell line, designated, D1.1 have been deposited with the American Type Culture Collection, 10801 University Blvd., Manassas, Va. 20110-2209, U.S.A., pursuant to the provisions of the Budapest Treaty on the International Recognition of the Microorganism Deposit for the Purposes of Patent Procedure and have been accorded ATCC Nos. HB 10916 and CRL 10915, respectively.

BRIEF DESCRIPTION OF THE FIGURES

FIGS. 1A–H. Cell surface phenotype of CD4− Jurkat D1.1. Shown are fluorescence histogram (FACS) analyses of CD4− Jurkat D1.1 and CD4+ Jurkat B2.7. The Y axis represents number of cells and the X axis represents relative fluorescence intensity.

FIG. 1A. A fluorescence histogram (FACS) analysis of CD4+ Jurkat B2.7 is shown. This figure is a "control" which represents the background staining in the absence of added primary mAb.

FIG. 1B. A fluorescence histogram (FACS) analysis of CD4− Jurkat D1.1 is shown. This figure is a "control" which represents the background staining in the absence of added primary mAb.

FIG. 1C. Fluorescence histogram (FACS) analysis of CD4+ Jurkat B2.7 stained with mAb OKT3 (anti-CD3).

FIG. 1D. Fluorescence histogram (FACS) analysis of CD4− Jurkat D1.1 stained with mAb OKT3 (anti-CD3).

FIG. 1E. Fluorescence histogram (FACS) analysis of CD4+ Jurkat B2.7 stained with mAb OKT4 (anti-CD4).

FIG. 1F. Fluorescence histogram (FACS) analysis of CD4– Jurkat D1.1 stained with mAb OKT4 (anti-CD4).

FIG. 1G. Fluorescence histogram (FACS) analysis of CD4+ Jurkat B2.7 stained with mAb W6/32 (anti-MHC I).

FIG. 1H. Fluorescence histogram (FACS) analysis of CD4– Jurkat D1.1 stained with mAb W6/32 (anti-MHC I).

FIGS. 2A–F. Jurkat D1.1 induces CD23 expression on resting B lymphocytes.

Shown are two-color FACS analyses of adherence depleted, high density B cells after 24 h of culture alone (media) or with CD4– Jurkat (D1.1) or CD4+ Jurkat (B2.7) by using anti-IgM-FITC or anti-CD20 (Leu-16)-FITC on the x axis and anti-CD23-PE on the y-axis (Becton-Dickinson).

The numbers shown in the upper right hand corner of each of the histograms in FIGS. 2A–F represents the percentage of all gated cells that express both molecules. In the experiment shown, single color FACS showed the population of small, high density B cells to be 2% CD3(OKT3)+, 84% IgM+, 84% CR2(HB-5)+, and 87% CD20(Leu-16)+.

FIG. 2A. Two-color FACS analysis of adherence depleted, high density B cells after 24 h of culture alone (media) by using anti-IgM-FITC on the x axis and anti-CD23-PE on the y-axis.

FIG. 2B. Two-color FACS analysis of adherence depleted, high density B cells after 24 h of culture alone (media) by using anti-CD20 (Leu-16)-FITC on the x axis and anti-CD23-PE on the y-axis.

FIG. 2C. Two-color FACS analysis of adherence depleted, high density B cells after 24 h of culture with CD4+ Jurkat (B2.7) by using anti-IgM-FITC on the x axis and anti-CD23-PE on the y-axis. The population of B cells cultured with Jurkat B2.7 expressed CD23 on 16% of IgM+ cells.

FIG. 2D. Two-color FACS analysis of adherence depleted, high density B cells after 24 h of culture with CD4+ Jurkat (B2.7) by using anti-CD20 (Leu-16)-FITC on the x axis and anti-CD23-PE on the y-axis. The population of B cells cultured with Jurkat B2.7 expressed CD23 on 16% of CD20+ cells.

FIG. 2E. Two-color FACS analysis of adherence depleted, high density B cells after 24 h of culture with CD4– Jurkat (D1.1) by using anti-IgM-FITC on the x axis and anti-CD23-PE on the y-axis. The population of B cells cultured with Jurkat D1.1 expressed CD23 on 66% of IgM+ cells.

FIG. 2F. Two-color FACS analysis of adherence depleted, high density B cells after 24 h of culture with CD4– Jurkat (D1.1) by using anti-CD20 (Leu-16)-FITC on the x axis and anti-CD23-PE on the y-axis. The population of B cells cultured with Jurkat D1.1 expressed CD23 on 69% of CD20+ cells.

FIGS. 3A–B. Dose response of D1.1-induced CD23 expression.

FIG. 3A. Shown are the percentage of IgM+ cells that express CD23 after 24 h culture with varying ratios of D1.1 or B2.7 cells or cell supernatants. Experimental conditions and two-color FACS analysis were as described for FIGS. 2A–2F except that the ratio of Jurkats added to $2 \times 10^5$ B cells was varied as shown. The background level (B cells alone) of CD23 expression of IgM+ cells was 12%. The B cell population was 65% IgM+ in this experiment.

FIG. 3B. Supernatants were obtained 48 h after $1 \times 10^+$ D1.1 or B2.7 cells were cultured in 1 ml of Iscove's modified Dulbecco medium/10% FCS and were passed through 0.2-μm filters before addition to the B cells.

FIGS. 4A–E. Jurkat D1.1 induces B cell proliferation in the presence of PHA.

Figure 4B:
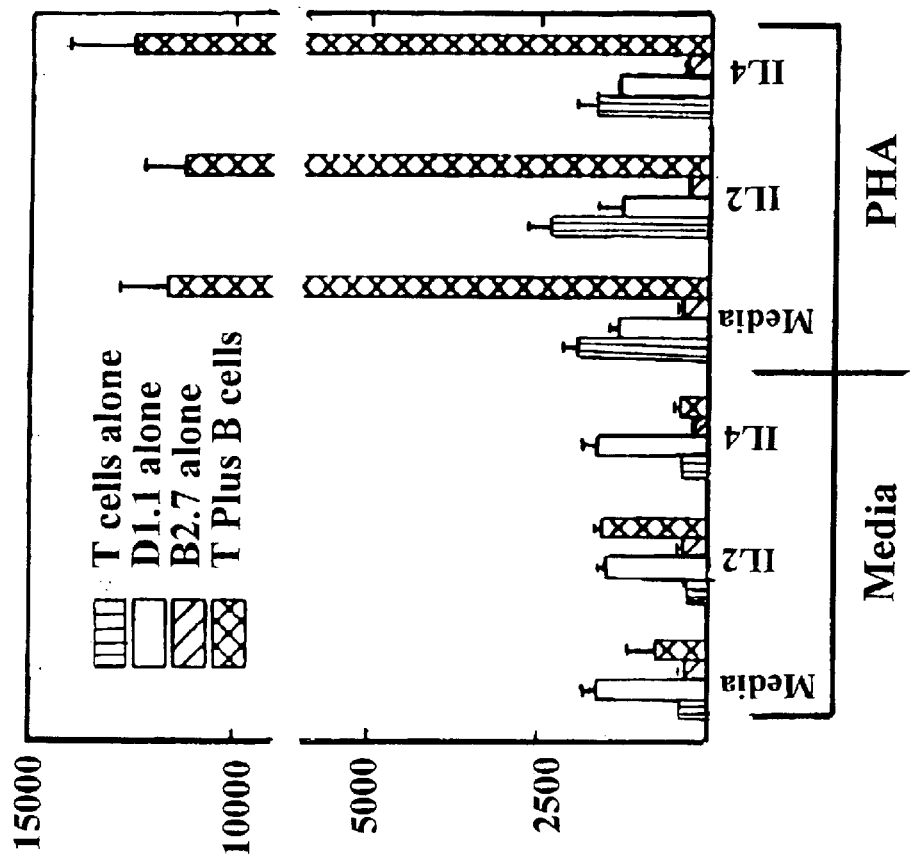
Figure 4A:
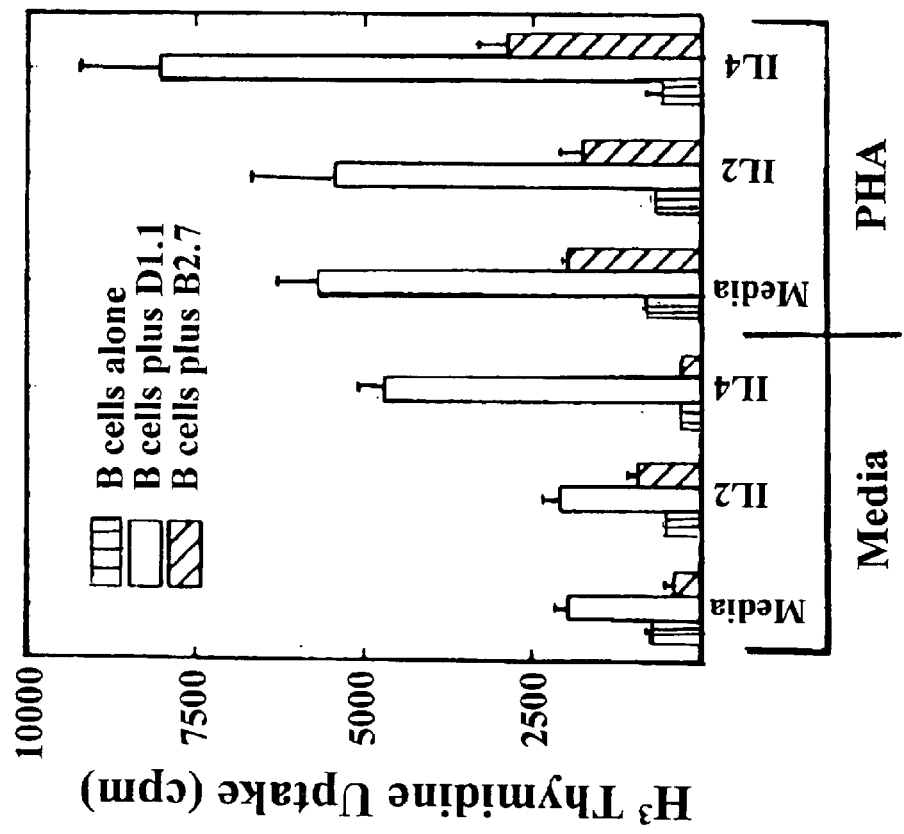

FIG. 4A. Shown is [$^3$H] thymidine uptake of B cells cultured with mitocycin-C-treated Jurkat cells in the presence of the indicated combinations of rIL-2 (25 U/ml), rIL-4 (25 U/ml), or PHA (5 μg/ml). Error bars represent standard deviation of the means of triplicate cultures.

FIG. 4B. Controls for the experiment shown in FIG. 4A.

Figure 5A:
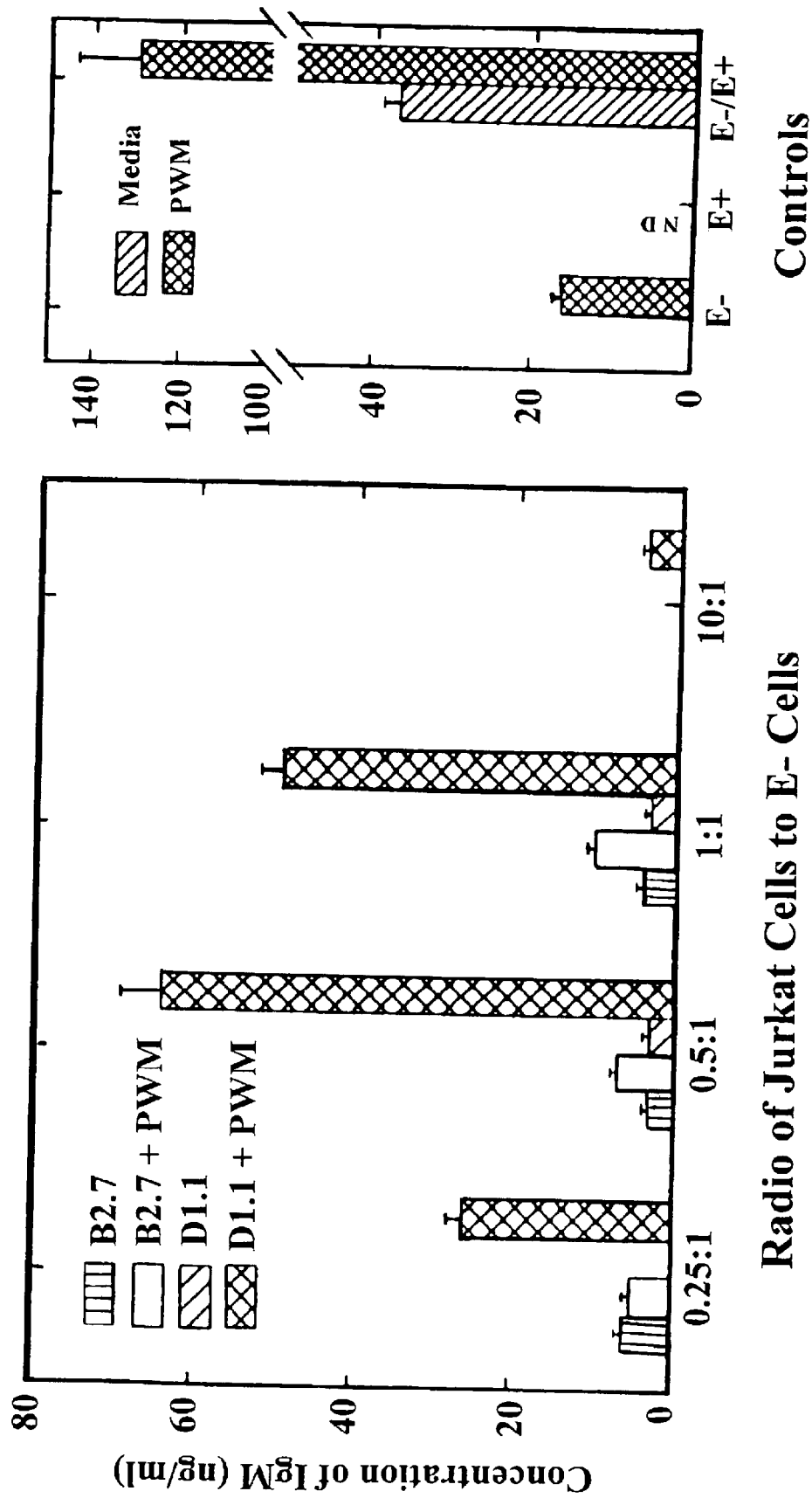
Figure 5B:
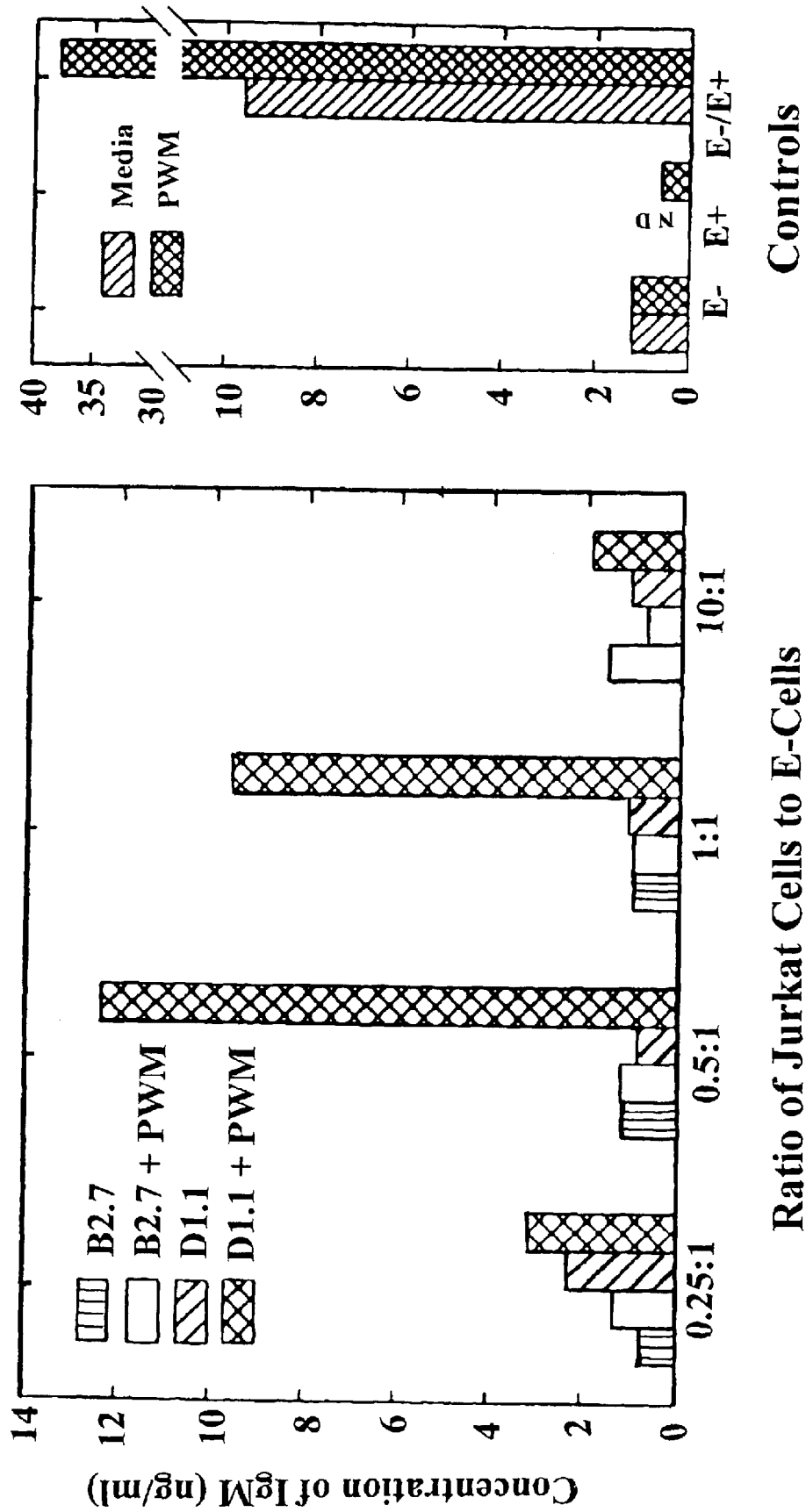

FIGS. 5A–C. Jurkat D1.1 induces B cell differentiation into Ig secreting cells.

E– cells are E rosette-depleted, adherence-depleted, high density Percoll population that is predominantly B cells. E+ cells are E rosette-positive, resting T cells treated with mitomycin-C. Measurement of Ig was performed by quantitative sandwich ELISA and error bars represent calculated standard deviation based on standard curves. E rosettes were performed with neuraminidase-treated sheep erythrocytes.

FIG. 5A. IgM in supernatants from the same experiments as in FIG. 5B. FIG. 5A-2 shows controls for the experiment shown in FIG. 5A-1.

FIG. 5B. Number of plaque-forming colonies per $10^6$ B cells induced by indicated ratios of Jurkat D1.1 or B2.7 to B cells in the presence of absence of PWM. FIG. 5B-2 shows controls for the experiment shown in FIG. 5B-1.

FIG. 5C. IgG in supernatants from the same experiments as in FIG. 5B. FIG. 5C-2 shows controls for the experiment shown in FIG. 5C-1.

FIGS. 6A–E. rIL-4 but not D1.1 increased B cell sIgM expression.

Shown are fluorescence histogram (FACS) analyses resulting from experiments similar to those in FIGS. 3A–B. The median channel fluorescence of IgM is shown on the right column.

Figure 6A:
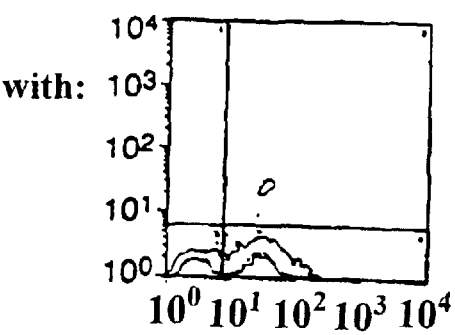

FIG. 6A. FACS analysis of B cells cultured with Jurkat B2.7.

Figure 6B:
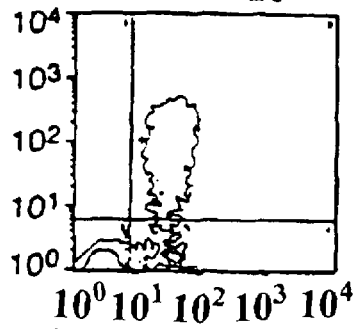

FIG. 6B. FACS analysis of B cells cultured with Jurkat D1.1.

Figure 6C:
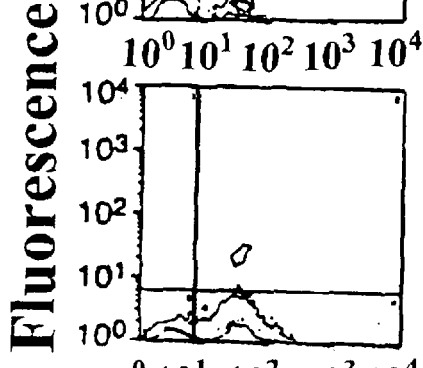

FIG. 6C. FACS analysis of B cells cultured with Jurkat rIL-2. The concentration of rIL-4 is 50 U/ml.

Figure 6D:
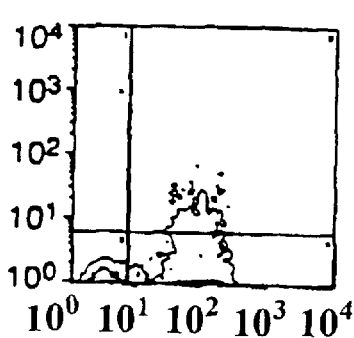

FIG. 6D. FACS analysis of B cells cultured with rIL-4. The concentration of rIL-4 is 50 U/ml.

Figure 6E:
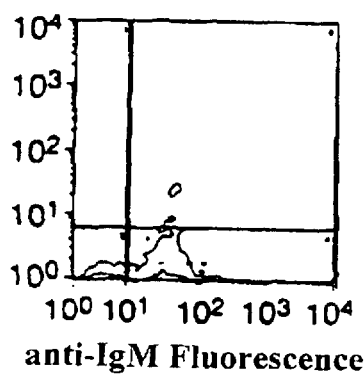

FIG. 6E. FACS analysis of B cells cultured with rIL-4+ anti-IL4. The concentration of anti-IL-4 shown is 1.25 μg/ml and the concentration of rIL-4 is 50 U/ml.

FIGS. 7A–L. Binding of mAb 5c8 to Jurkat D1.1 cells.

Shown are fluorescence histogram (FACS) analyses of CD4– Jurkat D1.1 and CD4+ Jurkat B2.7 cells. The Y axis represents number of cells and the X axis represents relative fluorescence intensity. FITC represents the background staining of an isotype matched control mAb.

FIG. 7A. A fluorescence histogram (FACS) analysis of CD4– Jurkat D1.1 cells.

FIG. 7B. A fluorescence histogram (FACS) analysis of CD4+ Jurkat B2.7 cells. FITC represents the background staining of an isotype matched control mAb.

FIG. 7C. A fluorescence histogram (FACS) analysis of CD4– Jurkat D1.1 cells stained with mAb OKT3(anti-CD3).

FIG. 7D. A fluorescence histogram (FACS) analysis of CD4+ Jurkat B2.7 cells stained with mAb OKT3(anti-CD3).

FIG. 7E. A fluorescence histogram (FACS) analysis of CD4– Jurkat D1.1 cells stained with mAb OKT4(anti-CD4).

FIG. 7F. A fluorescence histogram (FACS) analysis of CD4+ Jurkat B2.7 cells stained with mAb OKT4(anti-CD4).

FIG. 7G. A fluorescence histogram (FACS) analysis of CD4– Jurkat D1.1 cells stained with mAb OKT8(anti-CD8).

FIG. 7H. A fluorescence histogram (FACS) analysis of CD4+ Jurkat B2.7 cells stained with mAb OKT8(anti-CD8).

FIG. 7I. A fluorescence histogram (FACS) analysis of CD4– Jurkat D1.1 cells stained with mAb W6/32(anti-MHC I).

FIG. 7J. A fluorescence histogram (FACS) analysis of CD4+ Jurkat B2.7 cells stained with mAb W6/32(anti-MHC I).

FIG. 7K. A fluorescence histogram (FACS) analysis of CD4– Jurkat D1.1 cells stained with mAb 5c8.

FIG. 7L. A fluorescence histogram (FACS) analysis of CD4+ Jurkat B2.7 cells stained with mAb 5c8.

FIGS. 8A–E. Monoclonal antibody 5c8 inhibits Jurkat D1.1 induced CD23 expression by B Lymphocytes.

Shown are two color FACS analyses of adherence depleted, high density B cells after 24 h of culture using anti-IgM-FITC (the X axis) and anti-CD23-PE (on the Y axis).

The number in the upper right hand corner of the FACS tracings represents the percentage of IgM$^+$ cells that expressed CD23.

Figure 8A:
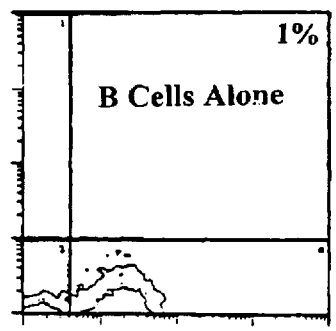

FIG. 8A. Two color FACS analyses of adherence depleted, high density B cells after 24 h of culture alone.

Figure 8B:
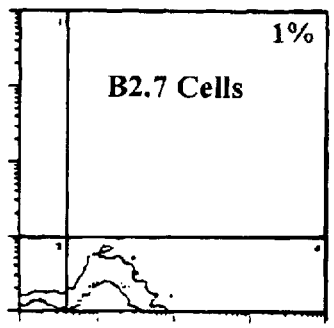

FIG. 8B. Two color FACS analyses of adherence depleted, high density B cells after 24 h of culture with the B2.7 Jurkat clones.

Figure 8C:
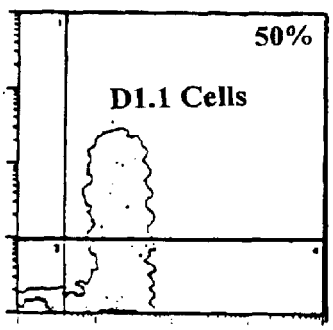

FIG. 8C. Two color FACS analyses of adherence depleted, high density B cells after 24 h of culture with the D1.1 Jurkat clones.

Figure 8D:
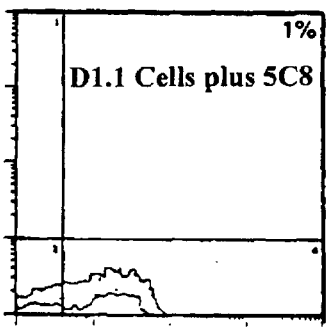

FIG. 8D. Two color FACS analyses of adherence depleted, high density B cells after 24 h of culture with the D1.1 Jurkat clones in the presence of mAb 5c8. The mAb 5c8 was present at a 1:200 dilution of hybridoma supernatant.

Figure 8E:
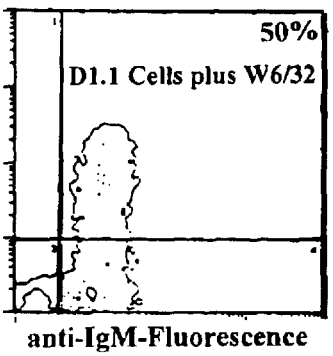

FIG. 8E. Two color FACS analyses of adherence depleted, high density B cells after 24 h of culture with the D1.1 Jurkat clones in the presence of W6/32. The mAb W6/32 was present at 1 µg/ml. The murine IgG2a mAb W6/32 recognizes a monomorphic determinant on Class I MHC molecules.

FIGS. 9A–B. SDS/PAGE analysis of surface proteins immunoprecipitated by mAb 5c8 and control mAbs.

FIG. 9A. Shown are autoradiograms of immunoprecipitates with mAb 5c8 or control mAbs from cells lysates of surface iodinated Jurkat D1.1 cells that were separated on 12.5% polyacrylamide in the presence (reduced, R) or absence (non-reduced, NR) of 2-ME (2-mercaptoethanol). mAbs shown are anti-CD28 (KOLT-4) and anti-MHC Class I (W6/32). MW markers represent the migration of pre-labelled standards. NMS: normal mouse serum.

FIG. 9B. Same as FIG. 9A except that Jurkat B2.7 cells were used in place of Jurkat D1.1 cells.

FIGS. 10A–L. Effects of T cell activation and metabolic inhibitors on the expression of 5c8 antigen on activated T cells.

FIG. 10A. FACS histogram of resting T cells using FITC. FITC represents a control for background staining.

FIG. 10B. FACS histogram of resting T cells using mAb 5c8.

FIG. 10C. FACS histogram of resting T cells using anti-CD69.

FIG. 10D. FACS histogram of activated T cells using FITC. T cells were activated by PMA (10 ng/ml) and PHA (10 µg/ml) for 5 h. FITC represents a control for background staining.

FIG. 10E. FACS histogram of activated T cells using mAb 5c8. T cells were activated by PMA (10 ng/ml) and PHA (10 µg/ml) for 5 h.

FIG. 10F. FACS histogram of activated T cells using anti-CD69. T cells were activated by PMA (10 ng/ml) and PHA (10 µg/ml) for 5 h.

FIG. 10G. FACS histogram of activated T cells using FITC. T cells were activated by PMA (10 ng/ml) and PHA (10 µg/ml) for 5 h performed in the presence of actinomycin D (10 µM). FITC represents a control for background staining.

FIG. 10H. FACS histogram of activated T cells using mAb 5c8. T cells were activated by PMA (10 ng/ml) and PHA (10 µg/ml) for 5 h performed in the presence of actinomycin D (10 µM).

FIG. 10I. FACS histogram of activated T cells using anti-CD69. T cells were activated by PMA (10 ng/ml) and PHA (10 µg/ml) for 5 h performed in the presence of actinomycin D (10 µM).

FIG. 10J. FACS histogram of activated T cells using FITC. T cells were activated by PMA (10 ng/ml) and PHA (10 µg/ml) for 5 h performed in the presence of cycloheximide (100 µM). FITC represents a control for background staining.

FIG. 10K. FACS histogram of activated T cells using mAb 5c8. T cells were activated by PMA (10 ng/ml) and PHA (10 µg/ml) for 5 h performed in the presence of or cycloheximide (100 µM).

FIG. 10L. FACS histogram of activated T cells using anti-CD69. T cells were activated by PMA (10 ng/ml) and PHA (10 µg/ml) for 5 h performed in the presence of cycloheximide (100 µM).

FIGS. 11A–F. Kinetics of expression of 5c8 on isolated CD4$^+$ or CD8$^+$ T cell subsets.

Shown is a fluorescence histogram of CD4$^+$ or CD8$^+$ cells at the indicated time points after freshly purified T cell subsets were activated with PHA (10 µg/ml) and PMA (10 ng/ml).

Solid line: 5c8 binding; dashed line: IgG2a control; and dotted line: anti-CD69.

Figure 11A:
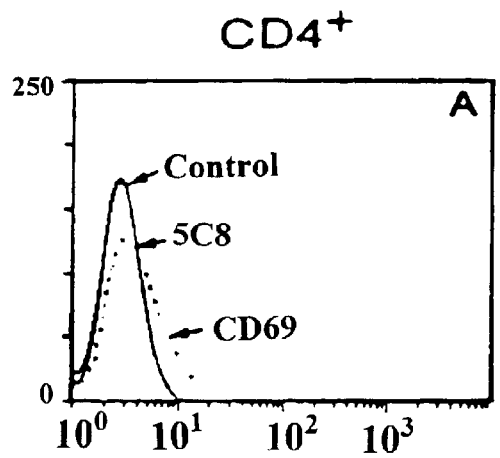

FIG. 11A. Fluorescence histogram of CD4$^+$ cells which were not activated with PHA (10 µg/ml) and PMA (10 ng/ml). Solid line: 5c8 binding; dashed line: IgG2a control; and dotted line: anti-CD69.

Figure 11B:
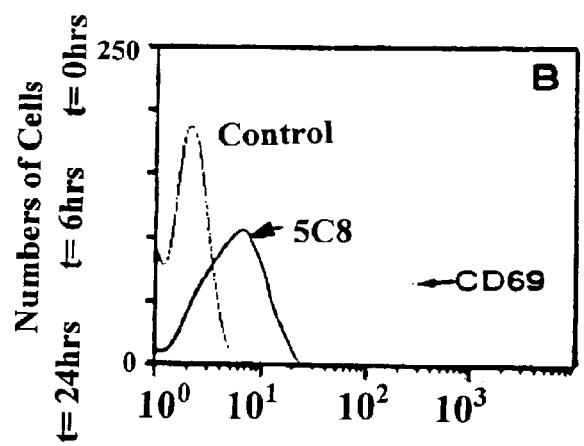

FIG. 11B. Fluorescence histogram of CD4$^+$ cells 6 hours after freshly purified T cell subsets were activated with PHA (10 µg/ml) and PMA (10 ng/ml).

Figure 11C:
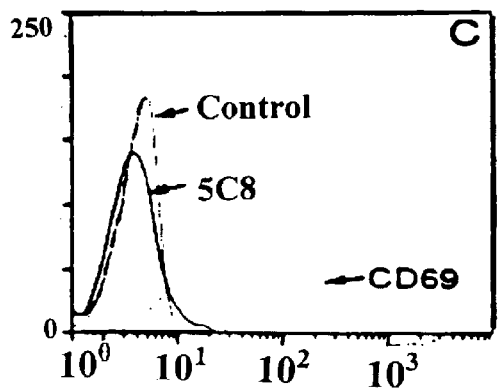

FIG. 11C. Fluorescence histogram of CD4$^+$ cells 24 hours after freshly purified T cell subsets were activated with PHA (10 µg/ml) and PMA (10 ng/ml).

Figure 11D:
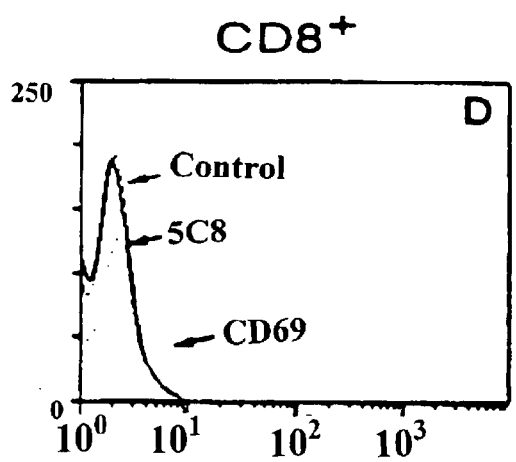

FIG. 11D. Fluorescence histogram of CD8$^+$ cells which were not activated with PHA (10 µg/ml) and PMA (10 ng/ml).

Figure 11E:
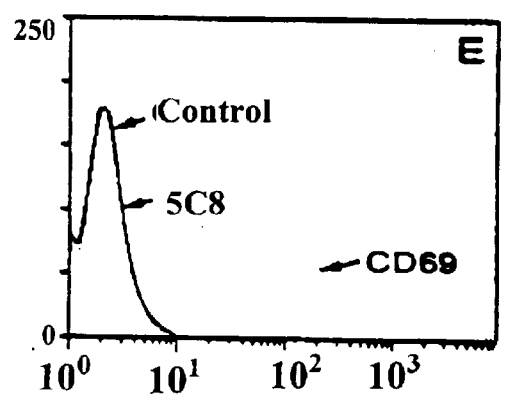

FIG. 11E. Fluorescence histogram of CD8$^+$ cells 6 hours after freshly purified T cell subsets were activated with PHA (10 µg/ml) and PMA (10 ng/ml).

Figure 11F:
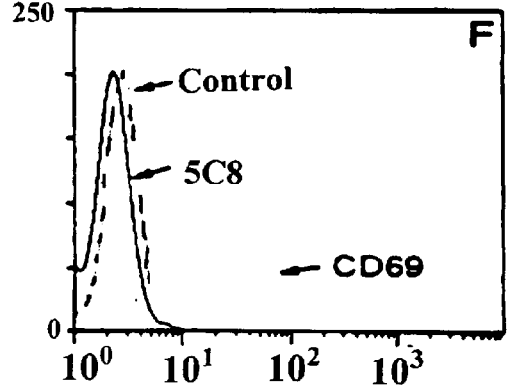

FIG. 11F. Fluorescence histogram of CD8$^+$ cells 24 hours after freshly purified T cell subsets were activated with PHA (10 µg/ml) and PMA (10 ng/ml).

DETAILED DESCRIPTION OF THE INVENTION

This invention provides a monoclonal antibody which specifically recognizes and forms a complex with a protein located on the surface of activated T cells, thereby inhibiting T cell activation of B cells. Activated T cells are found normally only in the germinal centers of an animal's lymph nodes. However, activated T cells are found in the peripheral blood of animals suffering from T cell tumors, e.g., T cell leukemias and lymphomas.

The monoclonal antibody described and claimed herein binds to T cells which are interacting with B cells in the germinal centers of lymph nodes and not to other T cells. Monoclonal antibodies known to those skilled in the art to specifically recognize and bind to proteins on the surface of T cells and thereby inhibit the activation of B cells, e.g., anti-CD28 monoclonal antibody and anti-LFA-1 monoclonal antibody, do not distinguish activated T cells.

For the purposes of this invention, "activated T cells" are T cells capable of providing T cell helper function to resting B cells. For the purposes of this invention, "germinal centers of lymph nodes" are the areas in lymph nodes where T cells provide T cell helper function to B cells.

For the purposes of this invention a "monoclonal antibody" is an antibody produced by a hybridoma cell. Methods of making monoclonal antibody-synthesizing hybridoma cells are well known to those skilled in the art, e.g, by the fusion of an antibody producing B lymphocyte with an immortalized B-lymphocyte cell line.

In one embodiment of this invention, the B cells are resting B cells. In another embodiment of this invention, the B cells are primed B cells. For the purposes of this invention, "resting" B cells are unactivated B cells, i.e., undifferentiated B cells which do not synthesize antibody molecules. For the purposes of this invention, "primed" B cells are B cells which have been contacted with antigen and have thereby been partially activated, but which do not yet synthesize antibody molecules.

In one embodiment of this invention, the monoclonal antibody is a murine monoclonal antibody. In another embodiment of this invention, the monoclonal antibody is a chimaeric monoclonal antibody. In still another embodiment of this invention, the monoclonal antibody is a humanized monoclonal antibody. However, in the preferred embodiment of this invention, the monoclonal antibody is a human monoclonal antibody.

For the purposes of this invention, a "chimaeric" monoclonal antibody is a murine monoclonal antibody comprising constant region fragments ($F_c$) from a different animal. In a preferred embodiment of this invention, the chimaeric monoclonal antibody comprises human $F_c$ and murine $F_{ab}$. For the purposes of this invention, a "humanized" monoclonal antibody is a murine monoclonal antibody in which human protein sequences have been substituted for all the murine protein sequences except for the murine complementarity determining regions (CDR) of both the light and heavy chains.

In one embodiment of this invention, the monoclonal antibody is directed to the protein to which the monoclonal antibody 5c8 (ATCC Accession No. HB 10916) is directed. In another embodiment of this invention, the monoclonal antibody is directed to the epitope to which the monoclonal antibody 5c8 (ATCC Accession No. HB 10916) is directed. In still another embodiment of this invention, the monoclonal antibody is the monoclonal antibody 5c8.

In one of this invention, the 5c8 antibody is labelled with a detectable marker, for example, a radioactive isotope, enzyme, dye or biotin. In another embodiment of this invention, the monoclonal antibody is conjugated to a therapeutic agent, for example, a radioisotope, toxin, toxoid or chemotherapeutic agent. In still another embodiment of this invention, the monoclonal antibody is conjugated to an imaging agent for example, a radioisotope.

This invention provides a pharmaceutical composition comprising the monoclonal antibody and a pharmaceutically acceptable carrier. For the purposes of this invention "pharmaceutically acceptable carriers" means any of the standard pharmaceutical carriers. Examples include, but are not limited to, physiological saline, phosphate buffered saline containing POLYSORB 80™ or water.

The monoclonal antibodies described and claimed herein are useful for isolating the proteins to which the monoclonal antibodies bind. The monoclonal antibodies are also valuable in new and useful methods for: inhibiting the immune response in an animal; imaging T cell tumors in an animal; detecting the presence of a T cell tumor in an animal; determining whether an animal harbors a T cell tumor; inhibiting the proliferation of T cell tumor cells in an animal suffering from a T cell cancer; and inhibiting viral infection of the T cells of an animal.

This invention provides an isolated nucleic acid molecule encoding the light chain protein of the monoclonal antibody. In one embodiment of this invention, the nucleic acid molecule is a DNA molecule. Preferably, the DNA molecule is a cDNA molecule.

The nucleic acid sequences described and claimed herein are useful for generating new viral and circular plasmid vectors described below. The nucleic acid molecules are also valuable in a new and useful method of gene therapy, i.e., by stably transforming cells isolated from an animal with the nucleic acid molecules and then readministering the stably transformed cells to the animal. Methods of isolating cells include any of the standard methods of withdrawing cells from an animal. Suitable isolated cells include, but are not limited to, bone marrow cells. Methods of readministering cells include any of the standard methods of readministering cells to an animal.

This invention provides a gene transfer vector, for example a plasmid or a viral vector, comprising a nucleic acid molecule encoding the light chain protein of the monoclonal antibody operably linked to a promoter of RNA transcription. This invention also provides a gene transfer vector, for example a plasmid or a viral vector, comprising a nucleic acid molecule encoding the heavy chain protein of the monoclonal antibody operably linked to a promoter of RNA transcription.

The gene transfer vectors described and claimed herein are valuable as products useful for generating stably transformed eukaryotic host cells, and thereby in new and useful methods of growing such host cells under conditions suitable for the production of a protein.

This invention provides a host vector system comprising the gene transfer vectors described and claimed herein in a suitable host cell. In one embodiment of this invention, the suitable host cell is a stably transformed eukaryotic cell, for example a stably transformed yeast or a mammalian cell. In the preferred embodiment of this invention, the stably transformed eukaryotic cell is a stably transformed mammalian cell.

The host vector system described and claimed herein is valuable in a new and useful method for the synthesis of a monoclonal antibody, comprising growing the host vector system under conditions suitable for the production of the monoclonal antibody.

This invention provides a hybridoma cell producing a monoclonal antibody of this invention. Preferably, the hybridoma cell is the hybridoma cell producing the monoclonal antibody 5c8 (ATCC Accession No.HB 10916). The hybridoma cells were accorded with ATCC Accession No. HB 10916 which was deposited on Nov. 14, 1991 with the American Type Culture Collection (ATCC), 10801 University Blvd., Manassas, Va. 20110-2209, U.S.A. under the provision of the Budapest Treaty on the International Recognition of the Deposit of Microorganisms for the Purposes of Patent Procedure. For the purposes of this invention, a "hybridoma cell" is a cell formed by the fusion of an immortalized cell and an antibody-producing cell, thereby forming a cell which makes a monoclonal antibody.

This invention provides a CD4⁻ human T cell leukemia cell line designated D1.1 (ATCC Accession No.CRL 10915) capable of constitutively providing contact-dependent helping function to B cells. The D1.1 cell was deposited on Nov. 14, 1991 with the American Type Culture Collection (ATCC), 10801 University Blvd., Manassas, Va. 20110-2209, U.S.A. under the provision of the Budapest Treaty for the International Recognition of the Deposit of Microorganisms for the Purposes of Patent Procedure. In one embodiment of this invention, the B cells are resting B cells. In another embodiment of this invention, the B cells are primed B cells.

The cell line described and claimed herein is valuable as a source of the isolated activated T cell surface protein, which is valuable for the information it provides concerning the nucleotide sequences which encode it. The nucleotide sequences are valuable in a new and useful method of producing the soluble activated T cell surface protein described and claimed herein. The cell line is also valuable in new and useful methods for immunizing an animal against a protein antigen and for screening pharmaceutical compounds for their ability to inhibit T cell activation of B cells.

This invention provides an isolated protein from the surface of activated T cells that is necessary for T cell activation of B cells. In one embodiment of this invention, the B cells are resting B cells. In another embodiment of this invention, the B cells are primed B cells. Preferably, the isolated protein is the protein to which the monoclonal antibody 5c8 (ATCC Accession No. HB 10916) binds.

This invention provides an isolated nucleic acid molecule encoding the T cell surface protein. In one embodiment of this invention, the nucleic acid molecule is a DNA molecule. Preferably, the DNA molecule is a cDNA molecule. The nucleic acid molecules are valuable as products for generating new viral and circular plasmid vectors described below. The nucleic acid molecules are also valuable in a new and useful method of gene therapy, i.e., by stably transforming cells isolated from an animal with the nucleic acid molecules and then readministering the stably transformed cells to the animal. Methods of isolating cells include any of the standard methods of withdrawing cells from an animal. Suitable isolated cells include, but are not limited to, bone marrow cells. Methods of readministering cells include any of the standard methods of readministering cells to an animal.

This invention also provides a gene transfer vector, for example a plasmid or a viral vector, comprising the isolated nucleic acid molecule encoding the actiavted T cell surface protein.

The gene transfer vectors described and claimed herein are valuable as products useful for generating stably transformed eukaryotic host cells, and thereby in new and useful methods of growing such host cells under conditions suitable for the production of a protein.

This invention further provides a host vector system comprising the gene transfer vector in a suitable host cell. In one embodiment of this invention, the suitable host cell is a stably transformed eukaryotic cell, for example, a stably transformed yeast or a mammalian cell. Preferably, the stably transformed cell is a stably transformed mammalian cell.

The host vector system is valuable as a product useful for the large scale synthesis of the activated T cell surface protein by growing the host vector system under conditions suitable for the production of protein. Thus, a method of producing the activated T cell surface protein is also provided. This invention further provides the protein produced by this method.

This invention provides an isolated, soluble protein from the surface of activated T cells necessary for T cell activation of B cells. In one embodiment of this invention, the B cells are resting B cells. In another embodiment of this invention, the B cells are primed B cells.

For the purposes of this invention, a "soluble protein" is a protein free of cell membranes and other cellular components. Preferably, the soluble protein is the protein to which the monoclonal antibody 5c8 (ATCC Accession No.HB 10916) binds. In one embodiment of this invention, the soluble protein is labeled with a detectable marker, for example, a radioactive isotope, enzyme, dye or biotin. The soluble protein is valuable as a product for making a new and useful pharmaceutical composition.

Thus, a pharmaceutical composition comprising the soluble protein and a pharmaceutically acceptable carrier is also provided. "Pharmaceutically acceptable carriers" means any of the standard pharmaceutically acceptable carriers. Examples include, but are not limited to, phosphate buffered saline, physiological saline, water and emulsions, such as oil/water emulsions.

This invention provides an isolated nucleic acid molecule encoding the soluble protein. In one embodiment of this invention, the nucleic acid molecule is a DNA molecule. Preferably, the DNA molecule is a cDNA molecule.

The nucleic acid sequences described and claimed herein are useful for generating new viral and circular plasmid vectors described below. The nucleic acid molecules are also valuable in a new and useful method of gene therapy, i.e., by stably transforming cells isolated from an animal with the nucleic acid molecules and then readministering the stably transformed cells to the animal. Methods of isolating cells include any of the standard methods of withdrawing cells from an animal. Suitable isolated cells include, but are not limited to, bone marrow cells. Methods of readministering cells include any of the standard methods of readministering cells to an animal.

This invention also provides a gene transfer vector, for example, a plasmid vector or a viral vector, comprising the isolated nucleic acid molecule operably linked to a promoter of RNA transcription.

The gene transfer vectors described and claimed herein are valuable as products useful for generating stably transformed eukaryotic host cells, and thereby in new and useful methods of growing such host cells under conditions suitable for the production of a protein.

This invention further provides a host vector system comprising the gene transfer vector in a suitable host cell. In one embodiment of this invention, the suitable host cell is a stably transformed eukaryotic cell, for example, a stably transformed eukaryotic yeast or mammalian cell. Preferably, the stably transformed cell is a stably transformed mammalian cell.

The host vector system is valuable as a product useful for the large scale synthesis of the soluble activated T cell surface protein by growing the host vector system under conditions suitable for the production of protein and recovering the protein so produced. Thus, a method of producing the soluble protein is also provided. This invention further provides the soluble protein produced by this method.

This invention provides a method of inhibiting B cell activation in an animal which comprises administering to the animal an effective inhibiting amount of a pharmaceutical composition comprising the monoclonal antibody which specifically recognizes the activated T cell surface protein and a pharmaceutically acceptable carrier. For the purposes of this invention, an "effective inhibiting amount" of a pharmaceutical composition is any amount of the pharmaceutical composition which is effective to bind to a protein on the surface of activated T cells and thereby inhibit T cell activation of B cells. In one embodiment of this invention, the B cells are resting B cells. In another embodiment of this invention, the B cells are primed B cells.

Methods of determining an "effective amount" are well known to those skilled in the art and will depend upon factors including, but not limited to, the type of animal involved and the animal's body weight. In one embodiment of this invention, the animal is a mammal, for example a mouse or a human. Preferably, the mammal is a human.

For the purposes of this invention, "administration" means any of the standard methods of administering a pharmaceutical composition known to those skilled in the art. Examples include, but are not limited to, intravenous, intraperitoneal or intramuscular administration.

The method of inhibiting B cell activation is valuable in a new and useful method for inhibiting the immune response of an animal. In one embodiment of this invention, the animal is a mammal, for example a mouse or a human. Preferably, the mammal is a human.

In one embodiment of this invention, inhibiting the immune response of an animal is valuable as a method of inhibiting the rejection by the animal of a transplant organ, for example, a heart, kidney or liver.

In another embodiment of this invention, inhibiting the immune response of an animal is valuable as a method of inhibiting the autoimmune response in an animal suffering from autoimmune disease. Examples of autoimmune diseases include, but are not limited to, rheumatoid arthritis, Myasthenia gravis, systemeic lupus erythematosus, Graves' disease, idiopathic thrombocytopenia purpura, hemolytic anemia, diabetes mellitus and drug-induced autoimmune diseases, e.g., drug-induced lupus.

In still another embodiment of this invention, inhibiting the immune response in an animal is valuable as a method of inhibiting allergic responses, e.g., hay fever or an allergy to penicillin, in the animal.

This invention provides a method of imaging T cell tumors, e.g., T cell leukemias or lymphomas, in a patient which comprises: administering to the patient an effective imaging amount of a pharmaceutical composition comprising the monoclonal antibody which specifically recognizes the activated T cell surface protein, conjugated to an imaging agent, under conditions permitting the formation of a complex between the monoclonal antibody and a protein on the surface of the tumor cells; and imaging any monoclonal antibody/protein complex formed, thereby imaging any T cell tumors in the patient. Preferably, the patient is a human patient.

The T cell surface protein is found in animals free of tumors only on the surface of activated T cells, i.e., those T cells providing contact-dependent helper function to B cells in the germinal centers of lymph nodes. However, the protein is found on the surface of T cell tumor cells circulating in the blood of the animal.

"Administering" means any of the standard methods of administering a pharmaceutical composition known to those skilled in the art. Examples include, but are not limited to intravenous, intramuscular or intraperitoneal administration. Methods of detecting the formation of monoclonal antibody/protein complexes, e.g., by exposure of x-ray film, are well known to those skilled in the art.

An "effective imaging amount" of the pharmaceutical composition is any amount effective for the formation of complexes between the monoclonal antibody and a cell surface protein, such that the complexes can be imaged. Methods of determining an "effective imaging amount" are well known to those skilled in the art and depend upon factors including, but not limited to the type of animal involved, the size of the animal and the imaging agent used. In one embodiment of this invention, the imaging agent is a radioisotope.

This invention provides a method of detecting the presence of a T cell tumor, e.g., a T cell leukemia or lymphoma, in an animal which comprises: administering to the animal an amount of a pharmaceutical composition comprising a monoclonal antibody bound to a detectable marker effective to bind to a protein on the surface of T cell tumor cells under conditions permitting the formation of complexes between the monoclonal antibody and the protein; clearing any unbound imaging agent from the animal; and detecting the presence of any monoclonal antibody/protein complex so formed, the presence of such complex indicating the presence of T cell tumor cells in the animal. In one embodiment of this invention, the animal is a mammal, e.g., a mouse or a human. Preferably, the mammal is a human.

"Administering" means any of the standard methods of administering a phramaceutical composition known to those skilled in the art. Examples include, but are not limited to intravenous, intramuscular or intraperitoneal administration. Methods of detecting the formation of monoclonal antibody/protein complexes, e.g., by exposure of x-ray film or microscopic examination, are well known to those skilled in the art.

An "effective amount" of the pharmaceutical composition is any amount of the pharmaceutical composition effective to detect the presence of a T cell tumor in the animal. Methods of determining an "effective amount" are well known to those skilled in the art and depend upon a number of factors including, but not limited to: the type of animal involved, the size of the blood sample contacted and the detectable marker used. In one embodiment of this invention, the detectable marker is a radiosotope, enzyme, dye or biotin.

This invention provides a method of determining whether an animal harbors a T cell tumor, e.g., a T cell leukemia or lymphoma, which comprises: isolating a sample of blood from the animal; contacting said sample with an amount of pharmaceutical composition comprising a monoclonal antibody, wherein the monoclonal antibody is labelled with a detectable marker, effective to bind to a soluble protein under conditions permitting the formation of a complex between the monoclonal antibody and the protein; and detecting the presence of any monoclonal antibody/protein complex so formed, the presence of such complex indicating the presence of T cell tumor cells in the patient.

The method provided by this invention is valuable as a new and useful method of detecting the presence of T cell tumor cells in the blood of an animal before the presence of the tumor cells themselves can be detected. The method provided by this invention is also valuable as a new and useful method for determining the effectiveness of the treatment of an animal with an anti-T cell tumor drug, i.e., by determining the level of soluble protein in the blood of the animal, such level being indicative of the effectiveness of the treatment.

It is well known to those skilled in the art that the blood of patients suffering from T cell tumors contains soluble proteins, e.g., the Tac antigen, shed from the surface of T cell tumor cells. Thus, the presence of soluble T cell surface proteins in the blood of an animal is indicative of the presence of T cell tumors in the animal.

For the purposes of this invention, a "soluble protein" is a protein free of cell membranes and other cellular components. In the preferred embodiment of this invention, the soluble protein is the protein to which the monoclonal antibody 5c8 (ATCC Accession No. HB 10916) binds.

"Isolating" blood from an animal means any of the generally acceptable methods of withdrawing blood and immediately placing the blood into a receptacle containing an anticoagulant, e.g., heparin, EDTA or citrate. Methods of detecting monoclonal antibody/protein complexes are well known to those skilled in the art. Examples include, but are not limited to, exposure of x-ray film and ELISA.

An "effective amount" of the pharmaceutical composition is any amount of the pharmaceutical composition effective to detect the presence of the soluble protein in the blood of the animal. Methods of determining an "effective amount" are well known to those skilled in the art and depend upon a number of factors including, but not limited to: the type of animal involved, the size of the blood sample contacted and the detectable marker used. In one embodiment of this invention, the detectable marker is a radiosotope, enzyme, dye or biotin.

In one embodiment of this invention, the animal is a mammal, e.g., a mouse or a human. Preferably, the mammal is a human.

This invention provides a method of inhibiting the proliferation of T cell tumor cells[ in an animal suffering from a T cell cancer, e.g., a T cell leukemia or lymphoma, which comprises administering to the patient an amount of the pharmaceutical composition, comprising a monoclonal antibody conjugated to a therapeutic agent, effective to inhibit the proliferation of T cell tumor cells. In one embodiment of this invention, the animal is a mammal, e.g., a mouse or a human. Preferably, the mammal is a human.

"Administering" means any of the standard methods of administering a phramaceutical composition known to those skilled in the art. Examples include, but are not limited to intravenous, intramuscular or intraperitoneal administration.

An "effective amount" of the pharmaceutical composition is any amount of the pharmaceutical composition effective to inhibit the proliferation of T cell tumor cells. Methods of determining an "effective amount" are well known to those skilled in the art and depend upon factors including, but not limited to: the type of animal involved, the size of the animal and the therapeutic agent used. In one embodiment of this invention, the therapeutic agent is a radioisotope, toxin, toxoid or chemotherapeutic agent.

This invention provides a method of inhibiting viral infection of the T cells of an animal by the HTLV I virus comprising administering to the animal an amount of a pharmaceutical composition, comprising a monoclonal antibody which specifically recognizes a protein on the surface of activated T cells, effective to inhibit the infection of T cells by the HTLV I virus. In one embodiment of this invention, the animal is a mammal, e.g., a mouse or a human. Preferably, the mammal is a human.

It is well known to those skilled in the art that the CD4 protein is the cellular protein to which the HTLV I virus binds. HTLV I virus thus specifically infects $CD4^+$, but not $CD8^+$ T cells. This invention provides a protein, the protein to which monoclonal antibody 5c8 binds, also specific to $CD4^+$ T cells.

This invention provides a method of screening a pharmaceutical compound, e.g., cyclosporin, cyclophosphamide or azothioprine, for its ability to inhibit T cell helper function which comprises: isolating a sample of blood from an animal; culturing said sample under conditions permitting activation of the B cells contained therein; contacting the sample with an amount of the D1.1 cell line effective to activate B cells; contacting the sample with an amount of a pharmaceutical compound effective to inhibit T cell activation of B cells if the pharmaceutical compound is capable of inhibiting T cell activation; and determining whether the T cell line activates B cells in the presence of the pharmaceutical compound.

In one embodiment of this invention, the B cells are resting B cells. In another embodiment of this invention, the B cells are primed B cells.

In one embodiment of this invention, the blood is isolated from a mammal, e.g., a mouse or a human.

"Isolating" blood from an animal means any of the generally acceptable methods of withdrawing blood and immediately placing the blood into a receptacle containing an anticoagulant, e.g., heparin, EDTA or citrate. Culturing B cells under "conditions permitting activation of B cells" comprises culturing B cells in the presence of lymphokines. An "effective activating amount" of the D1.1 cell line is any concentration of the cells in culture effective to activate B cells in the culture. Methods of determining an "effective activating amount" are well known to those skilled in the art.

A method of immunizing an animal against a protein antigen which comprises: isolating a sample of blood including immature B lymphocytes from the animal; recovering immature B cells from said sample; coculturing said immature B cells with an amount of the cell line D1.1 or the pharmaceutical composition comprising the soluble activated T cell surface protein effective to stimulate the B cells to differentiate under conditions permitting the differentiation of B cells; contacting said differentiated B cells with an amount of the protein antigen effective to induce the differentiated B cells to produce an antibody which recognizes the protein antigen; and administering said antibody-producing B lymphocytes to the animal from which the blood sample was isolated.

For the purposes of this invention, "immature B cells" are undifferentiated, non-antibody synthesizing B cells.

"Isolating" blood from an animal means any of the generally acceptable methods of withdrawing blood and immediately placing the blood into a receptacle containing an anticoagulant, e.g., heparin, EDTA or citrate. Culturing B cells under "conditions permitting differentiation of B cells" comprises culturing B cells in the presence of lymphokines. Methods of administering the B lymphocytes to the animal include any of the generally acceptable methods for administering cells to an animal.

An "effective amount" of the D1.1 cell line or the soluble activated T cell surface protein is any amount of the cell line or the soluble protein effective to induce B cells to differentiate. Methods of determining an "effective amount" are well known to those skilled in the art.

An "effective differentiating amount" of a protein antigen is any amount of the antigen effective to induce differentiated B cells to produce an antibody which specifically recognizes the antigen.

In one embodiment of this invention, the animal is a mammal, e.g., a mouse or a human. Preferably, the mammal is a human.

In one embodiment of the invention, the antigen is a viral protein antigen, e.g., a hepatitis B virus protein antigen, a Human T cell Leukemia Virus protein antigen or a human Immunodeficiency Virus protein antigen. In another embodiment of this invention, the antigen is an autoantigen.

This invention provides a method of treating a patient suffering from hypogammoglobulinemia which comprises administering to the patient an amount of the soluble activated T cell surface protein effective to treat the patient for hypogammoglobulinemia. Methods of determining an "effective amount" are known to those skilled in the art.

Materials and Methods

GENERATION AND CHARACTERIZATION OF 5C8 MONOCLONAL ANTIBODY. Five BALB/c mice were immunized with $2\times10^6$ D1.1 cells in saline intravenously and then boosted intraperitoneally at five, approximately two-week, intervals. The sera of these mice were titrated to test for the presence of antibodies that bound preferentially to Jurkat D1.1 versus B2.7 cells by FACS. One mouse, which showed the best differential titer, received a boost of $2\times10^6$ D1.1 cells intravenously 3 d prior to fusion. Splenocytes from this mouse were fused with $7\times10^7$ murine SP2/0 myeloma fusion partner cells as previously described (59). The cell mixture was cultured overnight in Dulbecco's Modified Eagle's Medium (DMEM) containing 15% FCS before the fusion product was seeded into 360 8-mm wells. Colonies appeared in 220 wells and all were screened by FACS for differential binding to D1.1 and B2.7 cells. A mAb designated 5c8 was found to bind to D1.1 cells and not B2.7 cells. The 5c8 clone was subcloned multiple times until monoclonality was established. The 5c8 mAb was found to be IgG2a by Elisa (HYCLONE®, Logan, Utah).

MONOCLONAL ANTIBODIES. The following mAbs were produced by hybridomas available from the American Type Culture Collection (Rockville, Md.): OKT11 (anti-CD2), OKT10(anti-38), OKT8(anti-CD8), OKT6(anti-CD1a), OKT4(anti-CD4), OKT3 (anti-CD3), OKT1(anti-CD5), 3A1(anti-CD7), Tac(anti-CD25), T-HB5(anti-CD21, CR2), W6/32(anti-MHC class I), AB2.06(anti-MHC class II), L243(anti MHC class II), 93F10(anti-MHC class II), TS1/22.1.13(anti-LFA-1a), TS1/18.1.2.11.4(anti-LFA-1β), TS2/9.1.4.3 (anti-LFA-3) and 187.1(anti-human Ig(Fab)). These mAbs were either used at saturating concentrations of hybridoma supernatants, or purified from ascites fluid on protein A columns (Biorad, Rockville Center, N.Y.). The anti-Jurkat TCR clonotypic (anti-v38) mAb 16G8 and a panel of other such anti-TCR mAb were purchased from Diversi-T, T Cell Science (Cambridge, Mass.). The mAb OKT4A was purchased from Ortho Pharmaceutical (Raritan, N.J.), TCRδ-1 was the gift of Dr. Michael Brenner, Harvard Medical School (Boston, Mass.). M241(anti-CD1c) was the gift of Dr. Cox Terhorst of Harvard Medical College. FITC labeled ant-CD23-PE mAbs and unlabelled anti-CD69 were purchased from Becton Dickinson (Mountainview, Calif.). FITC labeled anti-IgM was purchased from Tago (Burlingame, Calif.). Kolt-4 (anti-CD28) and anti-CD27 were purchased from Accurate Scientific (Westbury, N.Y.).

Recombinant proteins, rIL-4 was purchased from Genzyme (Cambridge, Mass.). rIL-2 was a gift of Hoffmann-LaRoche (Nutley, N.J.).

Cytofluorographic Analysis. Approximately $10^5$ cells were incubated with saturating concentrations of the indicated mAbs for 45 min at 4° C. in the presence of 80 μg/ml heat-aggregated human IgG (International Enzyme, Fallbrook, Calif.). Cells were washed to remove unbound mAb before incubation with goat anti-mouse Ig secondary antibody coupled to fluorescein (Cappel, Cochranville, Pa.).

For two color analysis, cells were reacted with the indicated directly coupled FITC or Phycoerythrin (PE) conjugated mAb for 45 min at 4° C. in the presence of aggregated human IgG. Prior to analysis, cells were washed and resuspended in PBS. Fluorescence intensity was measured on a FACSCAN Cytofluorograph with the consort-30 software (Becton-Dickinson, Mountainview, Calif.). In experiments involving co-culture of B cells with Jurkat clones, the Jurkat cells were excluded from the analysis of B cell fluorescence by gating on the distinct population of cells with low forward and side light scatter. In experiments with PMA and PHA activated cells, dead cells were excluded from analysis by treatment with propridium iodide and electronic FACS gating.

CELL LINES. The following cell lines are available from the American Type Culture Collection (Rockville, Md.): HPB-ALL, Jurkat, CEM, PEER, MOLT-IV, K562, Ramos, Raji and U937. BA is an Epstein Barr virus transformed B cell line that has been previously reported (60). H9 is available from the HIV Repository (Rockville, Md.). HLA typings was performed by Dr. Elaine Reed of the Department of Pathology, Columbia University (One Lambda, Los Angeles, Calif.). Jurkat D1.1 and B2.7 were negative for mycoplasma by the Mycotect kit (GIBCO®, Grand Island, N.Y.) and by the DNA hybridization method (Genprobe, La Jolla, Calif.).

ISOLATION OF CELL POPULATIONS. Peripheral blood lymphocytes were obtained from the freshly drawn blood of healthy volunteers by centrifugation on Ficoll-Hypaque (SIGMA®, St. Louis, Mo.) or Leukoprep (Becton-Dickson). T cells were positively selected with neuraminidase treated sheep erythrocytes. $CD4^+CD8^-$ and $CD4^-D8^{30}$ T cell subsets were isolated by anti-CD8 or anti-CD4 mAb treatment, respectively, followed by complement mediated lysis as previously described (19). B cells were derived from the population of cells that did not pellet through ficoll-hypaque after two rounds of rosetting with neuraminidase treated sheep erythrocytes.

B cells were further purified by either density centrifugation or by positive selection on an anti-Ig column. In the first method, E– cells were cultured overnight in polystyrene flasks (37° C., 5% $CO_2$) to deplete the macrophage by adherence. These non-T cell, non-macrophage cells were fractionated into high and low density fractions in a discontinuous 30%/50%/100% PERCOLL™ gradient by centrifugation at 2300 rpm for 12 min. High-low-density cells were obtained from the 50/100% interface and low-density cells from the 30/50% interface (62). The high density (resting) cells were typically 60–80% $CD20^+$, 55–80% $IgM^+$ and <5% $CD3^+$ and <5% $CD23^+$ (background). In other experiments (where indicated) B cells were purified by SEPHADEX® G-200 anti-P(ab)$_2$ Ig affinity chromatography into $sIg^+$ cells as has been described (19,62). The $sIg^+$ populations were typically <5% $CD3^+$, <10 $CD2^+$ and >90% $CD20^+$ when analyzed by FACS.

SDS POLYACRYLAMIDE GEL ELECTROPHORESIS. Jurkat clones were iodinated by the lactoperoxidase method, solubilized in 1% NP40, 25 mM Tris-Buffered PBS containing iodoacetamide and 10 μm PMSF. The cell lysates were reacted with protein A-4B SEPHAROSE™ beads (Pharmacia, Uppsula, Sweden) that were coated with mAb 187.1 (anti-human F(ab)Ig) and approximately 10 μg of the indicated mAb. After washing the beads to remove non-specifically bound proteins, the precipitated proteins were denatured by heating in SDS in the presence or absence of 2-ME. The denatured proteins and pre-stained MW markers (Biorad, Rockville Center, N.Y.) were electrophoresed through 12% polyacrylamide in 12 cm gels (Biorad Protean Gel, Rockville Center, N.Y.) and dried gels were used to expose X-ray film (Kodak, Rochester, N.Y.).

Mitomycin-C and Paraformaldehyde Treatments. Jurkat cells ($10^7$/ml) were treated with 50 μg/ml mitomycin-C (Sigma, St. Louis, Mo.) for 60 min at 37° C. The mitomycin-treated Jurkat cells were washed twice, resuspended in mitomycin free media and then cultured for 45–60 min at 3° C. The cells were washed two additional times and then added to the B cell cultures. In fixation experiments, T cells were treated with freshly made 0.5% paraformaldehyde for 5–10 minutes, quenched with 0.2 M L-lysine and washed five times before addition to cultures of B cells.

T CELL ACTIVATION. In experiments studying expression of 5c8 Ag, resting T cells were cultured in the presence or absence of 10 μg/ml phorbol myristate acetate (PMA) (Sigma, St. Louis, Mo.) and 10 μg/ml PHA (Sigma). In experiments studying the metabolic requirements for 5c8 Ag expression, T cells were activated in the presence of 100 μm cyclohexamide (Sigma) or 10 μg/ml actinomycin D (Sigma).

In experiments studying the induction of CD23 expression on high density B cells by activated T cells, the mAbs OKT3 or OKT4 were immobilized on the surfaces of 24 well culture plates by incubation of 10 μg/ml of mAb in PBS for 1 h. Control wells were incubated in PBS containing no mAb. After washing unbound mAb coated plates at $2 \times 10^6$ cell/well in the presence of 10 ng/ml phorbol dibutyrate (PDB) (Sigma) for 6 h. The cells were removed by vigorous pipetting, washed and fixed with 0.5% paraformaldehyde as described above before culture at a 1:1 ratio with $2 \times 10^5$ high density, PERCOLL® isolated, resting B cells for 18 h. B cell CD23 expression was determined by 2-color FACS as described above.

ASSAYS OF B CELL ACTIVATION AND DIFFERENTIATION. In experiments measuring the induction of B cell surface CD23 expression, $2 \times 10^5$ high density B cells were added to the indicated number of Jurkat cells or T cells in 200 μl of Iscove's Modified Dulbecco Medium (IMDM) 10% FCS round bottom microtiter wells (Nunc) and assayed for CD23 expression after 18–24 h. Two chamber experiments were performed with $5 \times 10^5$ Jurkat cells in the presence or absence of $5 \times 10^5$ B cells separated from $5 \times 10^5$ cells by 45-μm culture plate inserts from MILLIPORE(Bedford, Mass.).

B cell proliferation was measured by culturing $10^5$ B cells with equal numbers of mitomycin-C-treated E+ cells or Jurkat clones in flat bottom microtiter wells (NUNC™) in the presence or absence of PHA (5 μg/ml). The cultures were pulsed with 1 μCi ($H^3$) thymidine (New England Nuclear, Boston, Mass.) after 60 h and harvested 16 h later on glass fiber filter paper (Cambridge Technology, Watertown, Mass.). Beta scintillation cpm were measured on a beta counter (LKB RACKBETA™ counter, Model 1209).

The measurement of plaque forming colonies (PFC) was a modification of the Jerne hemolytic plaque assay (19). Briefly, $2.5 \times 10^5$ B cells were cultured with varying numbers of mitomycin-C treated Jurkat cells or untreated freshly isolated, autologous T cells for 6 days in the presence or absence of a 1:400 dilution of pokeweed mitogen (PWM) (GIBCO®, Grand Island, N.Y.). The cells were washed twice and resuspended in Hanks balanced salt solution. From an appropriate dilution, 50 ul of cultured cell suspension was mixed with; 10 μl of an 11% solution of SRBC that had been coated with rabbit anti-human Ig by chromic chloride, 10 μl of diluted rabbit anti-human Ig and 10 μl of guinea pig complement. These mixtures were introduced into duplicate glass chambers and cultured for 2h at 37° C. Plaques were counted using a dissecting microscope and expressed as plaque forming colonies (PFC) $10^6$ B cells.

ELISA for Ig isotype quantitation were performed by coating polystyrene 96-well plates (Immulon II, Dynatech Laboratories, Chantilly, Va.) with dilutions of goat anti-human IgA, IgG, or IgM (Tago, Burlingame, Calif.) in carbonate buffer, pH 9.6, for 18 h at 4° C. The plates were washed with 0.05% TWEEN® in PBS, and nonspecific sites were blocked by a 2h incubation of 1% BSA-PBS. After washing, 50 μl of cell culture supernatants or Ig isotype standards (Rockland, Gilbertsville, Pa.) were added to the wells and allowed to bind for 2 h. Next, goat anti-human Ig coupled to alkaline phosphatase (Tago) was added to detect bound human Ig. After 2 h, the wells were washed and p-nitrophenyl phosphate was added. Absorbance was measured at 405 nm in a Molecular Devices VMAX™ device (Palo Alto, Calif.). Samples were assayed in triplicate. Error bars represent calculated standard deviation from curve fit and interpolation (Delta-Soft, BioMetallics, Inc. Princeton, N.J.).

EXAMPLES

Example 1
Role of CD4 in T Cell Function

To study the role of CD4 in T cell functions, a CD4⁻ Jurkat clone (D1.1) was isolated from a culture that spontaneously developed a CD4⁻ subpopulation identified by a negative peak on FACS analysis. The lack of CD4 surface expression was relatively specific in that the cell surface phenotype of Jurkat D1.1 with respect to the binding of a large panel of mAb was similar to a CD4⁺ clone, Jurkat B2.7 (FIGS. 1A-H and Table 1). Although the differential expression of CD4 was the only qualitative difference between these subclones, some of the other molecular structures studied were expressed at quantitatively different levels. For example, Jurkat D1.1 expressed more CD2 and MHC class (HLA) molecules than Jurkat B2.7. However, Jurkat D1.1 expressed fewer CD28 molecules and fewer TCR-α/β(vβ8)/CD3 complexes than Jurkat B2.7 (FIGS. 1A-H and Table 1). In addition to their shared reactivity with the clonotypic anti-TCR mAb, Jurkat D1.1 and B2.7 were HLA identical (A3, 34,2, 16) and distinct from an unrelated T cell leukemic line, HPB-ALL (A9). Together, these data demonstrated that Jurkat D1.1 was a CD4⁻ subclone of Jurkat and that the absence of CD4 molecules was a relatively specific alteration in its surface phenotype.

TABLE 1

CELL SURFACE PHENOTYPES OF JURKAT CLONES D1.1 AND B2.7

| CD No. | Molecule | mAb | Mean Fluorescence Intensity[a] | |
|---|---|---|---|---|
| | | | D1.1 | B2.7 |
| | TCRα/β | BMA-031 | 10 | 40 |
| | TCRvβ8 | 16G8 | 30 | 70 |

TABLE 1-continued

CELL SURFACE PHENOTYPES OF JURKAT CLONES D1.1 AND B2.7

| CD No. | Molecule | mAb | Mean Fluorescence Intensity[a] | |
|--------|----------|-----|------|------|
| | | | D1.1 | B2.7 |
| | TCR-vβ5 | W6/32 | 0 | 0 |
| | MHC-classI | W6/32 | 190 | 70 |
| | MHC-classII | 2.06 | 0 | 0 |
| CD1a | T6 | OKT6 | 10 | 10 |
| CD1c | | M241 | 10 | 10 |
| CD2 | T11 | OKT11 | 100 | 10 |
| CD3 | TCR complex | OKT3 | 30 | 80 |
| CD4 | T4 | OKT4 | 0 | 130 |
| CD5 | T1 | OKT1 | 20 | 90 |
| CD7 | | 3A1 | 200 | 190 |
| CD8 | T8 | OKT8 | 0 | 0 |
| CD11a | LFA-1α | TS1/22.1.13 | 40 | 100 |
| CD14 | | My2 | 0 | 0 |
| CD16 | FcγRII | 3G8 | 20 | 20 |
| CD18 | LFA-1β | TS1/18.1.2.11.4 | 30 | 80 |
| CD21 | CR2 | HB-5 | 0 | 0 |
| CD23 | FcγRII | leu20 | 0 | 0 |
| CD25 | tac. IL-2Rα | tac | 0 | 0 |
| CD26 | DPPIV | taq-1 | 0 | 0 |
| CD28 | 9.3. gp44 | KOLT-4 | 30 | 70 |
| CD29 | | 4B4 | 140 | 110 |
| CD38 | T10 | OKT10 | 40 | 30 |
| CDw32 | FcγRII | 32.2 | 0 | 0 |
| CD45RA | T200. LCA | 2H4 | 30 | 40 |
| CD45RO | T200. LCA | UCHL1 | 10 | 20 |
| CDw49 | VLA-1 | 1B.3 | 0 | 0 |
| CD58 | LFA-III | TS2/9.1.4.3 | 40 | 60 |
| CD64 | FcγRI | IV 3 | 0 | 0 |

[a]Numbers represent mean fluorescence intensity (arbitrary units) as determined by FACS. Background is subtracted and numbers are rounded off to the nearest ten units.

In functional studies, we compared the ability of CD4+ (B2.7) and CD4− (D1.1) Jurkat cells to induce resting B cells to express CD23, a marker of B cell activation (32, 35, 57). Surprisingly, co-culture of B cells with CD4− Jurkat (D1.1) but not CD4+ Jurkat cells (B2.7) induced CD23 expression on greater than 60% of B cells (FIGS. 2A-F). The induction of B cell surface CD23 expression by Jurkat D1.1 was maximal at 20–24 h at a ratio of 1:1 D1.1 cells to B cells (FIGS. 3A-B). In contrast, the B3.7 Jurkat subclone did not activate B cells at high ratios (FIGS. 3A-B) or at long periods of coculture (up to 48 h, not shown). In addition, Jurkat D1.1 was unique in this ability compared with other T cell (H9, HPB-ALL, MOLT-IV, CEM) and non-T cell (U937) leukemic lines (not shown). Jurkat D1.1 induced B cell CD23 expression selectively because the levels of other B cell surface molecules such as IgM (FIGS. 2A-F), CD20 (FIGS. 2A-F), or class I MHC were not affected. The effect of Jurkat D1.1 on B cell activation was consistently observed on B cells from over 25 unrelated donors, suggesting that the effect was neither Ag nor MHC restricted.

B cell CD23 expression is an early and possibly intermediate stage in terminal B cell differentiation into Ig-secreting cells. Other stimuli, besides those contributed by activated T cell surfaces are required to mediate substantial B cell proliferation and differentiation. Because the measurements of B cell proliferation or differentiation require several days of culture, we inhibited the proliferation of the Jurkat clones by pretreatment with mitomycin-C, which did not abolish their capacity to activate B cells (Table 2).

TABLE 2

EFFECTS OF MITOMYCIN-C AND ANTIBODIES TO IL-4 ON B CELL CD23 EXPRESSION INDUCED BY JURKAT D1.1 CELLS

| B cells plus | C | rIL-4 | rIL-2 | Jurkat clones | | | |
|---|---|---|---|---|---|---|---|
| | | | | D1.1 | B2.7 | D1.1/M | B2.7/M |
| | 14 | 64 | 17 | 81 | 16 | 57 | 14 |
| Anti-IL-4 | ND | 28 | ND | 84 | ND | 64 | ND |
| Anti-IL-2 | ND | 60 | ND | 86 | ND | 60 | ND |

Shown are the percentages of CD20(Leu-16)− B cells expressing CD23 as determined by two-color FACS analysis with anti-CD20(Leu-16)-FITC and anti-CD23 PE. High density Percoll ®-fractionated B cells ($2 \times 10^4$) were cultured alone or with an equal number of either Jurkat B2.7 or D1.1 cells as indicated for 20 h. Where indicated, purified polyclonal rabbit anti-IL-4 or anti-IL-2 Ig was added at the initiation of the experiment to final concentrations of 1.25 µg/ml. Where indicated, rIL-2 or rIL-4 were added to indicated cultures to final concentrations of 25 U/ml. Cells analyzed were gated by forward and side light scatter to exclude the larger D1.1 or B2.7 cells (when present) from the analysis.
C: Control; D1.1/M: D1.1 cells treated with mitomycin-C; B2.7/M: B2.7 cells treated with mitomycin-C; ND: not determined.

Mitomycin-C treated CD4− Jurkat D1.1 and CD4+ Jurkat B2.7 were then studied for their ability to induce B cell proliferation or terminal B cell differentiation into Ig-secreting cells. In the presence of T cell-dependent B cell mitogens (ES), Jurkat D1.1+ but not B2.7-induced B cell proliferation measured by DNA synthesis (FIGS. 4A-B) and differentiation to Ig-secreting cells measured by reverse hemolytic plaque assay (FIG. 5A). In addition, the isotype of secreted antibody was characterized by quantitative ELISA. Jurkat D1.1 but not B2.7 induced the secretion of IgG and to a lesser extent, IgM into the culture supernatant (FIGS. 5B and C). Taken together, these data show that Jurkat D1.1 but not Jurkat B2.7 shared with activated T cells the functional capacity to support B cell differentiation and the secretion of IgM and IgG.

Example 2
Role of Diffusible Factors in B Cell Activation

D1.1 supernatants did not induce B cell CD23 expression (FIGS. 3A-B). We next performed two chamber experiments in which resting B cells were cultured in a chamber that was separated by a permeable membrane from either lymphokine containing media or from cultures of D1.1 cells in the presence or absence of B cells. In an experiment in which B cells (66% IgM+) were cultured in a chamber with a 0.45-mµ membrane, rIL-4 (25 U/ml) induced CD23 expression on 28% of IgM+ B cells as measured by two-color FACS analysis. In contrast, D1.1 cells did not activate B cells in the other chamber to express CD23 (4.7% for D1.1 vs 4.0% background). In addition, coculture of D1.1 cells with B cells in one chamber did not activate B cells in the other chamber to express CD23 (4.9%). However, D1.1 cells potently induced CD23 expression by the B cells with which they could establish direct contact (76% vs 8.4% for B2.7 cells). Taken together, these data failed to support a role for diffusible factors in mediating the D1.1 effect on B cells.

Because rIL-4 was known to activate B cells to express CD23 (66), we further studied the potential role of IL-4 in mediating this effect in addition to inducing CD23 expression on B cells. rIL-4 was known to up-regulate B cell sIgM+ expression (58). Whereas rIL-4 induced CD23 expression and sIgM up-regulation in a dose-dependent manner, D1.1 cells induced CD23 expression but did not up-regulate B cell sIgM (FIGS. 6A-E). The effect of D1.1 cells on B cell proliferation was also distinct from that of rIL-4 (FIGS. 4A-B). D1.1 cells, but not rIL-4 induced B cell proliferation in the presence of PHA. Interestingly, rIL-4 and D1.1 cells collaborated to induce B cell proliferation in the absence of PHA and augment D1.1 induced proliferation in the presence of PHA. Taken together these data suggest that the effect of D1.1 cells on B cells are distinct from those induced by IL-4. However, to directly examine the role of IL-4 in D1.1's effect on B cells, we used neutralizing antibodies to IL-4. Concentrations of anti-IL-4 antibodies that inhibited both the CD23 induction and sIgM up-regulation mediated by rIL-4 (FIGS. 6A-E) did not inhibit D1.1-mediated B cell CD23 expression (Table II). These data demonstrated that IL-4 alone did not account for the effect of D1.1 on B cells. Taken together, these results strongly suggested that cell-cell contact and not secreted factors accounted for the effects of D1.1 on B cell activation.

To substantiate the idea that cell-cell contact mediated the D1.1 effect on B cells, we fixed Jurkat D1.1 and control, B2.7 cells with 1% paraformaldehyde. Although paraformaldehyde fixation decreased the potency of Jurkat D1.1 to activate B cells, fixed D1.1 cells remained competent to induce B cell CD23 expression whereas, fixed B2.7 cells did not alter CD23 expression from the background level. At a ratio of 5:1 fixed D1.1 cells:B cells, 63% of B cells were induced to express CD23 as compared with 80% for unfixed D1.1 cells. Taken together, these data suggest that that surface structures on Jurkat D1.1 are sufficient to induce B cell activation.

Example 3

Characterization of Cell Surface Proteins on Activated CD4+ T Cells that Mediate Helper Effector Function In order to characterize cell surface proteins on activated CD4+ T cells that mediate helper effector function, mice were immunized with the D1.1 clone of Jurkat that possess contact dependent helper effector function. Monoclonal antibodies (mAb) are generated and hybridoma supernatants are screened for differential binding to the D1.1 clone and a non-helper Jurkat clone, B2.7.

A murine IgG2a mAb, termed 5c8, was identified that bound specifically to the surface of D1.1 cells and not to the surface of the non-helper, B2.7 cells (FIGS. 7A-L). The mAb 5c8 did not bind to a variety of other cell lines including: the T cell leukemia lines, CEM, H9, Molt-4 and Peer; the B cell derived cell lines, BA, Raji or Ramos; the myelomonocytic cell line, U937; or the erythroleukemia cell line, K562 (see Table 3 below).

TABLE 3

EXPRESSION OF 5c8 Ag ON CELL POPULATIONS AND CELL LINES

|  | Resting | Activated |
| --- | --- | --- |
| Cell Lines |  |  |
| Jurkat D1.1 | + | + |
| Jurkat B2.7 | − | − |
| CEM | − | − |
| H9 | − | ND |
| Molt-4 | − | − |
| PEER | − | − |
| BA | − | ND |
| Raji | − | ND |
| Ramos | − | ND |
| U937 | − | − |
| K562 | − | ND |

TABLE 3-continued

EXPRESSION OF 5c8 Ag ON CELL POPULATIONS AND CELL LINES

|  | Resting | Activated |
| --- | --- | --- |
| Cell Populations |  |  |
| T cells | − | + |
| B cells | − | − |
| Monocytes | − | − |

These data derive from FACS analyses of mAb 5c8 binding to the indicated cell lines or cell populations. The presence of mAb 5c8 binding was determined relative to FACS staining of appropriate positive and negative control mAbs for each cell line or population.
Nd: Not determined.

To assess whether mAb 5c8 reacts with a molecule that is functionally relevant to the helper capacity of the Jurkat clone D1.1, the effect of mAb 5c8 was studied in assays of D1.1 induced CD23 expression on B cells. The mAb 5c8 potently inhibited Jurkat D1.1 induced cell activation (FIGS. 8A-E). In contrast, the isotype control mAb, W6/32 did not inhibit D1.1 mediated B cell activation. The data presented here suggest that the 5c8 Ag plays a critical role in the helper effector function of D1.1 cells.

Example 4

Biochemical Characterization of the Antigen Recognized by mAb 5c8

In order to biochemically characterize the antigen recognized by mAb 5c8, immunoprecipitations were performed with mAb 5c8 or control mAbs that recognized Class I MHC (W6/32) or CD28 (Kolt-4) antigens on cell lysates of surface iodinated Jurkat D1.1 cells and control, non-helper Jurkat B2.7 cells that lack surface mAb 5c8 binding. The mAb 5c8 immunoprecipitated a protein that migrated on SDS/PAGE at 30 kDa from lysates of the helper clone D1.1 but not from the control B2.7 lysates (FIGS. 9A-B)

The protein species immunoprecipitated by mAb 5c8 was not affected by reduction with 2-mercaptoethanol (2-ME) suggesting that the 30 kDa band was neither a disulfide linked homodimer nor disulfide linked to another protein that was not accessible to iodination. In contrast, the control, anti-CD28 mAb, KOLT-4 immunoprecipitated (FIGS. 9A-B) an 88 kDa band in the absence of 2-ME and a 44 kDa band in the presence of 2-ME that is consistent with published reports (63) and with the interpretation that this structure is a disulfide linked homodimer. The control mAb W6/32 precipitated a non-disulfide linked heterodimer of 43 and 12 kDa MW proteins (FIGS. 9A-B). These data suggested that the mAb 5c8 recognized a 30 kDa MW non-disulfide linked protein species from the surface of D1.1 cells.

Example 5

Characterization of the Expression of 5c8 Ag by Normal Lymphoid Cells

The binding of mAb 5c8 or a variety of control mAb is studied by FACS on freshly isolated, T and B lymphocytes, monocytes and PMA and PHA stimulated T cells. Although, resting T or B lymphocytes or monocytes did not express 5c8 Ag (see Table 3 above and FIG. 10), a subset of activated T cells was found to express 5c8 Ag, 5 h after activation with PMA and PIIA (FIGS. 10A-L).

To characterize the kinetics and cellular distribution of 5c8 Ag expression, the binding of mAb 5c8 to T cells was studied by FACS at various intervals after T cell activation. The CD69 molecule, which is a 32/28 KDa disulfide linked heterodimer, was selected as a control because it is known to be induced rapidly on virtually all T cells after T cell activation (64). Whereas 5c8 was absent from resting T cells and was expressed on a subset of T cells following activation, in contrast, low level CD69 expression was present on resting T cells and high level CD69 expression was induced by activation on the entire T cell population (FIGS. 10A-L). The kinetics of expression further distinguished 5c8 Ag from CD69 because mAb 5c8 binding was significant 3 h after activation (64) and persisted for over 24 h (FIGS. 11A-F). The data presented here distinguish the 5c8 Ag from CD69 both by the cellular distribution of their expression and by the kinetics of their up-regulation following activation.

To determine if mRNA or protein synthesis is required for 5c8 Ag expression, T cells are stimulated by PMA and PHA in the presence or absence of Actinomycin D or cycloheximide and the expression of 5c8 and CD69 was compared. The expression of 5c8 was inhibited by either actinomycin D or cycloheximide treatment (FIGS. 10A-L). In contrast, CD69 was up-regulated by activation despite the presence of actinomycin D or cycloheximide (FIGS. 11A-F), as has been reported previously (64). These data suggested that the expression of the 5c8 antigen after T cell activation depends on transcription of mRNA and de novo protein synthesis.

Example 6

Characterization of the Subset of T Cells that Express 5c8 Ag After Activation

In order to characterize the subset of T cells that expressed 5c8 Ag after activation, CD4$^+$CD8$^-$ or CD4$^-$CD8$^+$ T cell populations were isolated by anti-CD8 or anti-CD4 mAb treatment, respectively, followed by complement depletion. The CD4$^+$CD8$^-$ or CD4$^-$CD8$^+$ populations were activated with PHA and PMA and studied for 5c8 Ag or CD69 expression by FACS. After activation, 5c8 expression was induced exclusively on CD4$^+$ cells and not on CD8$^+$ cells, despite the fact that CD8$^+$ cells expressed similar levels of CD69 after activation (FIGS. 11A-F). Taken together, these data demonstrated that 5c8 Ag expression is restricted to activated CD4$^+$ cells.

Example 7

Evaluation of the Role of 5c8 Ag in T Helper Function Mediated by Normal T Cells To evaluate the role of 5c8 Ag in T helper function mediated by normal T cells, the effect of mAb 5c8 was studied on the ability of activated T cells to induce small resting B cells to express surface CD23 molecules. T cells were cultured on surfaces that were coated with anti-CD3 (OKT3) or control, anti-CD4(OKT4) mAbs in the presence of phorbol dibutyrate (PBD) and then fixed with paraformaldehyde. These fixed T cells were studied for B cell activating capacity in the presence of soluble mAb 5c8 or OKT4. The mAb OKT4 was selected as an isotype matched control in these experiments because OKT4 reacts with T cell surface CD4 molecules but does not inhibit T-B interactions (19). The mAb 5c8, but not OKT4 inhibited the ability of activated T cells to induce B cell CD23 expression (see Table 4 below)

TABLE 4

EFFECT OF mAb 5C8 TREATMENT ON
B CELL SURFACE CD23 INDUCTION MEDIATED
BY PARAFORMALDEHYDE FIXED, ACTIVATED T CELLS.

|  | Media | mAb 5c8 | OKT4 |
| --- | --- | --- | --- |
| No T cells | 6.8 | ND | ND |
| Jurkat D1.1 | 93.8 | 9.8 | 96.1 |
| PDB-activated T cells | 29.8 | ND | ND |
| PDB/OKT4-activated T cells | 26.0 | ND | ND |
| PDB/OKT3-activated T cells | 52.7 | 30.4 | 56.1 |

Shown are the percentages of IgM$^+$ B cells that expressed CD23 by 2-color FACS analysis after B cells were cultured alone or in the presence of equal number of Jurkat D1.1 cells or paraformaldehyde fixed T cells that had been stimulated with PBD alone or in the presence of either immobilized anti-CD3 (OKT3) or anti-CD4(OKT4) mAbs, as indicated. The IgG2a mAbs, 5c8 and OKT4 were present at 500 ng/ml which is twice the concentration of mAb 5c8 that inhibited 90% of CD23 induction in a parallel dose response experiment.
ND: Not determined.

The effect of mAb 5c8 was next compared to that of OKT4 for its ability to inhibit terminal B cell differentiation driven by normal human T cells. In these experiments, CD4$^+$ T cells were cultured with autologous, column isolated B cells in the presence of PWM and the number of Ig secreting B cell plaque forming colonies (PFCS) was measured by reverse hemolytic plaque assay. The mAb 5c8, but not OKT4, inhibited the CD4$^+$ cell driven PFC response (see Table 5 below). Taken together, these data demonstrated that the 5c8 Ag mediates a contact dependent aspect of the helper effector function of activated CD4$^+$ T cells.

TABLE 5

EFFECT OF mAb 5C8 TREATMENT ON
THE INDUCTION OF ANTIBODY FORMING CELLS

| T cells | B cells | PWM | mAb | PFC | | |
| --- | --- | --- | --- | --- | --- | --- |
| | | | | Exp.1 | Exp.2 | Exp.3 |
| | B | | | 120 | 240 | 600 |
| | B | PWM | | 240 | 600 | 4,800 |
| CD4$^+$T | | | | 240 | 120 | 180 |
| CD4$^+$T | B | | | 2,580 | 780 | ND |
| CD4$^+$T | | PWM | | 3,840 | 240 | 60 |
| CD4$^+$T | B | PWM | | 149,760 | 85,200 | 25,800 |
| CD4$^+$T | B | PWM | 5c8 | 58,000 | 4,680 | 9,000 |
| CD4$^+$T | B | PWM | OKT4 | 143,520 | 103,200 | 30,960 |

Shown are the results of three separate experiments on unrelated donors in which CD4$^+$T cells were cultured in a 0.6:1 ratio with autologous, anti-Ig column isolated B cells in the presence or absence of PWM. The number of plaque forming colonies (PFC) per 106 B cells was measured by reverse hemolytic plaque assay. The mAbs 5C8 and OKT4 were present at 500 ng/ml except in experiment 1, in which OKT4 was present at 1 ug/ml.
ND: Not determined.

Discussion

The Jurkat D1.1 clone is functionally distinct from CD4+ Jurkat and from a variety of other leukemic T cell lines in that it induced B cells from a variety of unrelated subjects to express surface CD23 molecules, a marker of B cell activation and to proliferate and terminally differentiate into ISC in the presence of T-dependent B cell mitogens. The effect of D1.1 on B cell activation required intimate cellular contact and could not be accounted for by secreted factors or by IL-4 in particular. The fact that Jurkat D1.1 was able to induce contact dependent B cell activation and differentiation suggested that Jurkat D1.1 shares surface structure(s) with activated T cells that mediate the contact-dependent, effector phase of help.

The molecular interactions between activated T cells and B cells that mediate the effector phase of T helper function is complex and poorly understood. To dissect the mechanism of T helper effector function, several studies have measured early events in B cell differentiation. First, B cell synthesis of RNA, DNA and enzymes associated with cell cycle progression are induced by activated but not resting T cells (6,8,9,11,13–18). Second, B cell activation, measured by the induction of B cell surface CD23, is induced by activated but not resting T cells (13). Third, B cell activation and proliferation can be induced by activated T cells that have been fixed with paraformaldehyde (13,17). Fourth, B cell proliferation is induced by membrane preparations from activated but not resting T cells (9,12,33). Finally, the ability of activated T cells or activated T cell membranes to induce B cell activation or proliferation is abrogated by protease treatment (12,16). Taken together, these observations are consistant with the idea that T cell activation is associated with the induction of a surface structure that interacts with B cells and provides a contact dependent signal for B cell activation and proliferation. Similar to activated T cells, but unlike other leukemic cell lines, Jurkat D1.1 had the capacity to induce B cell CD23 expression in a manner that depended on cell-cell contact but was independent of lymphokines, Ag specificity or MHC restriction. The induction of B cell surface CD23 expression appears to be an early or intermediate stage in T-directed B cell differentiation into Ig secreting cells that can be driven by the surfaces of fixed, activated T cells (13,14). In addition to inducing B cell CD23 expression, Jurkat D1.1 was functionally distinct from CD4$^+$ Jurkat clones in that D1.1 induced terminal B cell differentiation in the presence of PWM. In these respects, Jurkat D1.1 appears to have acquired surface features that it shares with activated T cells and that stimulate B cells.

The nature of the structure on Jurkat D1.1 that accounts for helper function was not identified in the present work. Because CD28 molecules on T cells bind a B cell ligand (34), it was of particular interest to compare the expression of CD28 on the helper D1.1 and non-helper B2.7 clones. However, the fact that both Jurkat D1.1 and B2.7 expressed CD28 molecules demonstrated that CD28 alone, could not account for the unique functional properties of Jurkat D1.1. Moreover, in antibody blocking studies using mAb specific for CD2, CD3, CD5, CD38, LFA-1a, LFA-1b and LFA-3; we were unable to identify mAbs that inhibited D1.1 mediated B cell activation (not shown). In order to identify the distinctive cell surface features of D1.1 that mediate helper effector function, we initiated an attempt to generate mAbs that react with D1.1 and inhibit D1.1's ability to help B cells.

Although the surface structures that mediate helper function were not identified, the D1.1 system is instructive with respect to the role of CD4 molecules in helper effector function. It is curious that a Jurkat subclone isolated for being CD4– possessed helper function, which is normally associated with the subset of T cells that express CD4 molecules (14,35). Several lines of investigation have suggested that CD4 molecules do not play a direct role in helper effector function (2,8–12). However, the fact that both TCR and CD4 are known to interact with MHC Class II molecules (Ia) (36) have suggested that ligation of Ia molecules might be a model for helper effector function. In addition, the observation that ligation of Ia molecules on B cells can signal B cells has further supported this model (37–39). The fact that Jurkat D1.1 had helper function but was CD4– strongly suggests that CD4 molecules are not required for the effector phase of helper function. On the contrary, the finding that a CD4– clone of Jurkat has acquired helper function suggests that CD4 molecules might inhibit the helper effector function of CD4+ Jurkat cells. In order to directly determine the relationship between the lack of CD4 molecules on Jurkat D1.1 and its unique helper function, we have generated stable CD4+ transfectants of D1.1 by electroporation of CD4 cDNA constructs driven by heterologous promoters. The expression of CD4 did not inhibit the ability of D1.1 transfectants to activate B cells, suggesting that D1.1's helper activity is mediated by surface features other than the lack of CD4 molecules.

Recently it has been shown in the murine system that membrane preparations derived from activated, but not resting T lymphocytes are sufficient to induce B cell proliferation but not Ig secretion (9,12,33). The relevance of these studies to the D1.1 system is presently unclear, but it will be of interest to determine if membranes isolated from D1.1 cells induce B cell CD23 expression, proliferation and terminal differentiation. In any case, it is likely that Jurkat D1.1 will be useful for the identification and characterization of surface molecules important in mediating contact dependent helper function.

The functionally unique Jurkat leukemic line (D1.1) with constitutive, contact dependent helper function was utilized to generate a murine mAb, designated 5c8, that inhibited D1.1 induced B cell activation. The mAb 5c8 recognized a unique protein species on D1.1 cells that was not disulfide linked and migrated at 30 kDa MW on SDS/PAGE. On normal lymphoid cells, the expression of 5c8 Ag was restricted to a subset of T lymphocytes after activation. The activation induced expression of 5c8 Ag on T cells required transcription of mRNA and de novo protein synthesis. The 5c8 Ag was found to be transiently expressed on activated T cells with peak expression at 6 h and loss of expression by 24 h. The expression of 5c8 Ag was restricted exclusively to activated CD4+ T cells. In functional studies on normal T cells, the mAb 5c8 inhibited the ability of fixed, activated T cells to induce B cell CD23 expression. In addition, mAb 5c8 inhibited the ability of normal T cells to direct B cell differentiation. Taken together, these data demonstrate that the 5c8 Ag is a novel activation-induced surface protein expressed exclusively on activated CD4+ T cells that is involved in mediating a contact dependent element of T helper function.

The tissue distribution, kinetics of expression, metabolic requirements for induction and biochemistry of the 5c8 Ag distinquished the 5c8 Ag from other known surface proteins induced by T cell activation. First, all other known T cell activation markers (e.g. CD69, CD25, Ia) are expressed by both CD4+ and CD8+ T cells whereas the 5c8 Ag is expressed exclusively by CD4+ T cells. Second, the kinetics of 5c8 Ag expression following T cell activation were distinct from that of other T cell activation molecules. Whereas 5c8 Ag was maximally expressed 6 h after activation and absent 24 h after activation, CD25 (66), Ia (67,68) and the 32 kD form of CD27 (69) are induced 18 h or more after activation. In addition, CD69 is expressed more rapidly than 5c8 Ag and (unlike 5c8 Ag) persists for over 24 h. Third, 5c8 Ag was distinguished from CD69 by the metabolic requirements of their induction, because induction of 5c8 Ag but not CD69 expression depended on mRNA transcription and protein synthesis. Fourth, the 5c8 Ag was a 30 kD, non-disulfide linked species. In contrast, the early activation molecule, CD69 is a 28/32 kD disulfide linked heterodimer (65). Taken together, these data suggest that the 5c8 Ag was distinct from other known T cell activation molecules.

The 5c8 Ag was also distinguished from other T cell surface molecules that are known to play roles in T-B interactions by several aspects of their tissue distribution and biochemistry. First, 5c8 Ag was induced by T cell activation but was not expressed on resting cells. In contrast, CD4, CD2, CD5, CD28, LFA-1, ICAM-1, CD45RO and 6C2, which interact with B cell surface ligands (70–78) are expressed on resting T cells (77–82). Second, the specific expression of 5c8 Ag on activated T lymphocytes and not on B cells, monocytes or the panel of cell lines (Table 1.) distinguished 5c8 Ag from ICAM-1, CD4, CD5, LFA-1, CD2 and 6C2 molecules which are also expressed on either monocytes, B cells or certain of the cell lines (not shown). Third, the expression of 5c8 Ag was restricted to CD4$^+$ T cells whereas CD2, CD5, CD28, LFA-1, ICAM-1, CD45RO and 6C2 are expressed on CD8+ as well as CD4+ cells (77–82). Fourth, the 30 kD protein precipitated by mAb 5c8 is unlike any of these other proteins (77–82). Finally, 5c8 Ag was distinct from these other molecules because the mAb 5c8 was identified by its ability to inhibit the helper effector function mediated by Jurkat D1.1.

Because the mAb 5c8 inhibits the contact dependent helper effects of Jurkat D1.1 and fixed, activated T lymphocytes, it is likely that the 5c8 Ag mediates a B cell activating function by interacting with a ligand (or "counter-receptor") on the surfaces of B cells. The interaction of 5c8 Ag with a B cell counter receptor may mediate helper function either by providing additional adhesive forces to T-B pairs, transducing a stimulatory signal to B cell cytoplasms or by a combination of these mechanisms. Regardless of the precise mechanism, the transient expression of 5c8 Ag may provide a molecular solution to limiting non-specific B cell activation. We envision that the transient expression of 5c8 Ag in the localized milieu of antigen specific cognate T-B pairs may channel the antigen/MHC unrestricted activating function of 5c8 Ag to appropriate B cell targets. The kinetics of expression and down-regulation of 5c8 Ag are shared by the endothelial cell, activation induced, cell surface mediator of leukocyte and lymphocyte binding, ELAM-1 (83). This similarity might indicate that the strategy of utilizing transient expression to effect localized intercellular interactions may be shared by 5c8 Ag, ELAM-1 and potentially other, yet uncharacterized, surface molecules that transmit potent signals to other cells by direct contact.

The CD4 molecule identifies the population of T cells that contains precursors of T cells with helper function (4). However, the CD4+ subset is functionally heterogeneous and contains cytotoxic and suppressor cells in addition to helper cells (84,85). The fact that 5c8 Ag is involved in helper function suggests that 5c8 Ag may correlate more closely with the helper phenotype than CD4 expression. The heterogeneous distribution of 5c8 expression on activated CD4+ cells suggests that functional subsets of CD4+ T cells might be distinguished by their level of 5c8 expression. For example, it will be of interest to determine the functional potential of 5c8– and 5c8+ CD4+ T cells with respect to helper or cytotoxic activity.

T cell helper effector function is a complex process resulting in B cell responsiveness (22,54–56), regulation of isotype switching (86) and somatic hypermutation (87). The fact that T cells interact with B cells by a number of cell-cell interactions as well as by secreting various lymphokines suggests that individual signals or certain combinations of signals may regulate specific aspects of B cell differentiation. The fact that the mAb 5c8 inhibits a contact dependent aspect of T cell helper function provides a means of further dissecting the processes by which CD4$^+$ T cells regulate the humoral immune response.

REFERENCES

1. Mitchell, G. F. and J. F. Miller. 1968. Cell to cell interaction in the immune response. II. The source of hemolysin-forming cells in irradiated mice given bone marrow and thymus or thoracic duct lymphocytes. *J. Exp. Med.* 128:821.
2. Mitchison, N. A. 1971. The carrier effect in the secondary response to hapten-protein conjugates. V. Use of antilymphocyte serum to deplete animals of helper cells. *Eur. J. Immunol.* 1:68.
3. White, R. A., D. W. Mason, A. F. Williams, G. Galfre, and C. Milstein. 1978. T-lymphocyte heterogeneity in the rat: separation of functional subpopulations using a monoclonal antibody. *J. Exp. Med.* 148:664.
4. Reinherz, E. L., P. C. Kung, G. Goldstein, and S. F. Schlossman. 1979. Separation of functional subsets of human T cells by a monoclonal antibody. *Proc. Natl. Acad. Sci. U.S.A.* 76:4061.
5. Janeway, C. A., S. Carding, B. Jones, J. Murray, P. Portoles, R. Rasmussen, J. Rojo, K. Saizawa, J. West, and K. Bottomly 1988. CD4$^+$ T cells: specificity and function. *Immunol. Rev.* 101:39.
6. O'Brien, R. L., P. Marrack, U. Storb, and J. W. Kappler. 1988. B cells expressing Ig transgenes respond to a T-dependent antigen only in the presence of Ia-compatible T cells. *J. Immunol.* 141:3335.
7. Rahemtulla, A., W. P. Fung-Leung, M. W. Schilham, T. M. Kundig, S. R. Sambhara, A. Narendran, A. Arabian, A. Wakeham, C. J. Paige, R. M. Zinkernagel, R. G. Miller, and T. W. Mak. 1991. Normal development and function of CD8$^+$ cells but markedly decreased helper cell activity in mice lacking CD4. *Nature* 353:180.
8. Grusby, M. J., R. S. Johnson, V. E. Papaioannou, and L. H. Glimcher. 1991. Depletion of CD4$^+$ T cells in major histocompatibility complex class II-deficient mice. *Science* 253:1417.
9. Noelle, R. J. and E. C. Snow. 1991. T helper cell-dependent B cell activation. *FASEB J.* 5:2770.
10. Vitetta, E. S., R. Fernandez Botran, C. D. Myers, and V. M. Sanders. 1989. Cellular interactions in the humoral immune response. *Adv. Immunol.* 45:1.
11. Noelle, R. J. and E. C. Snow. 1990. Cognate interactions between helper T cells and B cells. *Immunol. Today* 11:361.
12. Katz, D. H., T. Hamaoka, M. E. Dorf, and B. Benacerraf. 1973. Cell interactions between histoincompatible T and B lyphocytes. The H-2 gene complex determines successful physiologic lymphocyte interactions. *Proc. Natl. Acad. Sci. U.S.A.* 70:2624.
13. Zinkernagle, R. M. 1976. T helpers may be sensitized by antigen-specifically altered structures, which are coded by the I region of the H-2 gene complex. *Adv. Exp. Med. Biol.* 66:527.
14. Sprent, J. 1978. Restricted helper function of Fl hybrid T cells positively selected to heterologous erythrocytes in irradiated parental strain mice. II. Evidence for restrictions affecting helper cell induction and T-B collaboration, both mapping to the K-end of the H-2 complex. *J. Exp. Med.* 147:1159.
15. Sprent, J. 1978. Role of H-2 gene products in the function of T helper cells from normal and chimeric mice in vivo. *Immunol. Rev.* 42:108.
16. Jones, B. and C. A. Janeway. 1981. Cooperative interaction of B lymphocytes with antigen-specific helper T lymphocytes is MHC restricted. *Nature* 292:547.
17. Julius, M. H., J. M. Chiller, and C. L. Sidman. 1982. Major histocompatibility complex-restricted cellular interactions determining B cell activation. *Eur. J. Immunol.* 12:627.
18. Chestnut, R. W. and H. M. Grey. 1981. Studies on the capacity of B cells to serve as antigen-presenting cells. *J. Immunol.* 126:1075.

19. Rogozinski, L., A. Bass, E. Glickman, M. A. Talle, G. Goldstein, J. Wang, L. Chess, and Y. Thomas. 1984. The T4 surface antigen is involved in the induction of helper function. *J. Immunol.* 126:735.
20. Sanders, V. M., J. M. Snyder, J. W. Uhr, and E. S. Vitetta. 1986. Characterization of the physical interaction between antigen-specific B and T cells. *J. Immunol.* 137:2395.
21. Snow, E. C., R. J. Noelle, J. W. Uhr, and E. S. Vitetta. 1983. Activation of antigen-enriched B cells. II. Role of linked recognition in B cell proliferation to thymus-dependent antigens. *J. Immunol.* 130:614.
22. Krusemeier, M. and E. C. Snow. 1988. Induction of lymphokine responsiveness of hapten-specific B lymphocytes promoted through an antigen-mediated T helper lymphocyte interaction. *J. Immunol.* 140:367.
23. Kupfer, A. and S. J. Singer. 1989. Cell biology of cytotoxic and helper T cell functions: immunofluorescence microscopic studies of single cells and cell couples. *Annu. Rev. Immunol.* 7:309.
24. Noelle, R. J., J. McCann, L. Marshall, and W. C. Bartlett. 1989. Cognate interactions between helper T cells and B cells. III. Contact-dependent, lymphokine-independent induction of B cell cycle entry by activated helper T cells. *J. Immunol.* 143:1807.
25. Bartlett, W. C., A. Michael, J. McCann, D. Yuan, E. Claassen, and R. Noelle. 1989. Cognate interactions between helper T cells and B cells. II. Dissection of cognate help by using a class II-restricted, antigen-specific, IL-2-dependent helper T cell clone. *J. Immunol.* 143:1745.
26. Kupfer, A., S. L. Swain, and S. J. Singer. 1987. The specific direct interaction of helper T cells and antigen-presenting B cells. II. Reorientation of the microtubule organizing center and reorganization of the membrane-associated cytoskeleton inside the bound helper T cells. *J. Exp. Med.* 165:1565.
27. Thomas, Y., J. Sosman, L. Rogozinski, 0. Irigoyen, P. C. Kung, G. Goldstein, and L. Chess. 1981. Functional analysis of human T cell subsets defined by monoclonal antibodies. III. Regulation of helper factor production by T cell subsets. *J. Immunol.* 126:1948.
28. Reinherz, E. L., P. C. Kung, J. M. Breard, G. Goldstein, and S. F. Schlossman. 1980. T cell requirements for generation of helper factor(s) in man: analysis of the subsets involved. *J. Immunol.* 124:1883.
29. Noelle, R. J., E. C. Snow, J. W. Uhr, and E. S. Vitetta. 1983. Activation of antigen-specific B cells: role of T cells, cytokines, and antigen in induction of growth and differentiation. Proc. Natl. Acad. Sci. U. S. A. 80:6628.
30. Thompson, C. B., M. E. Schaefer, F. D. Finkelman, I. Scher, J. Farrar, and J. J. Mond. 1985. T cell-derived B cell growth factor(s) can induce stimulation of both resting and activated B cells. *J. Immunol.* 134:369.
31. Clement, L. T., M. K. Dagg, and G. L. Gartland. 1984. Small, resting B cells can be induced to proliferate by direct signals from activated helper T cells. *J. Immunol.* 132:740.
32. Crow, M. K., J. A. Jover, and S. M. Friedman. 1986. Direct T helper-B cell interactions induce an early B cell activation antigen. *J. Exp. Med.* 164:1760.
33. Brian, A. A. 1988. Stimulation of B-cell proliferation by membrane-associated molecules from activated T cells. *Proc. Natl. Acad. Sci. U.S.A.* 85:564.
34. Hirohata, S., D. F. Jelinek, and P. E. Lipsky. 1988. T cell-dependent activation of B cell proliferation and differentiation by immobilized monoclonal antibodies to CD3. *J. Immunol.* 140:3736.
35. Jover, J. A., E. K. Chartash, B. Kushner, S. M. Friedman, and M. K. Crow. 1989. T helper cell-induced CD23 (BLAST-2) expression: an activation marker for the high density fraction of human B cells. *Clin. Immunol. Immunopathol.* 53:99.
36. Whalen, B. J., H. P. Tony, and D.C. Parker. 1988. Characterization of the effector mechanism of help for antigen-presenting and bystander resting B cell growth mediated by Ia-restricted Th2 helper T cell lines. *J. Immunol.* 141:2230.
37. Pollok, K. E., V. O'Brien, L. Marshall, J. W. Olson, R. J. Noelle, and E. C. Snow. 1991. The development of competence in resting B cells. The induction of cyclic AMP and ornithine decarboxylase activity after direct contact between B and T helper cells. *J. Immunol.* 146:1633.
38. Bartlett, W. C., J. McCann, D. M. Shepherd, M. Roy, and R. J. Noelle. 1990. Cognate interactions between helper T cells and B cells. IV. Requirements for the expression of effector phase activity by helper T cells. *J. Immunol.* 145:3956.
39. Martinez, A. C. and A. Coutinho. 1981. B-cell activation is a two step process. *Nature* 290:60.
40. Andersson, J., M. H. Schreier, and F. Melchers. 1980. T-Cell-dependent B-cell stimulation is H-2 restricted and antigen dependent only at the resting B-cell level. *Proc. Natl. Acad. Sci. U.S.A.* 77:1612.
41. Principato, M. A., G. S. Thompson, and S. M. Friedman. 1983. A cloned major histocompatibility complex-restricted trinitrophenyl-reactive human helper T cell line that activates B cell subsets via two distinct pathways. *J. Exp. Med.* 158:1444.
42. Goldberg, D., A. Green, A. B. Gottlieb, M. K. Crow, A. Lewison, and S. M. Friedman. 1985. Cloned allospecific human helper T cell lines induce an MHC-restricted proliferative response by resting B cells. *J Immunol.* 135:1012.
43. DeFranco, A. L., J. D. Ashwell, R. H. Schwartz, and W. E. Paul. 1984. Polyclonal stimulation of resting B lymphocytes by antigen-specific T lymphocytes. *J. Exp. Med.* 159:861.
44. Julius, M. H. and H. G. Rammensee. 1988. T helper cell-dependent induction of resting B cell differentiation need not require cognate cell interaction. *Eur. J. Immunol.* 18:375.
45. Julius, M. H., H. G. Rammensee, M. J. Ratcliffe, M. C. Lamers, J. Langhorne, and G. Kohler. 1988. The molecular interactions with helper T cells which limit antigen-specific B cell differentiation. *Eur. J. Immunol.* 18:381.
46. Riedel, C., T. Owens, and G. J. Nossal. 1988. A significant proportion of normal resting B cells are induced to secrete immunoglobulin through contact with anti-receptor antibody-activated helper T cells in clonal cultures. *Eur. J. Immunol.* 18:403.
47. Owens, T. 1988. A noncognate interaction with anti-receptor antibody-activated helper T cells induces small resting murine B cells to proliferate and to secrete antibody. *Eur. J. Immunol.* 18:395.
48. Cambier, J. C. and M. H. Julius. 1988. Early changes in quiescent B cell physiology subsequent to cognate and bystander interaction with helper T cells. *Scand. J. Immunol.* 2759.
49. Tohma, S. and P. E. Lipsky. 1991. Analysis of the mechanism of T cell-dependent polyclonal activation of human B cells. Induction of human B cell responses by fixed activated T cells. *J. Immunol.* 146:2544.
50. Lohoff, M., M. Dirks, P. Rohwer, and M. Rollinghoff. 1989. Studies on the mechanism of polyclonal B cell stimulation by Th2 cells. *Eur. J. Immunol.* 1977.

51. Friedman, S. M., M. K. Crow, 0. H. Irigoyen, C. Russo, D. N. Posnett, and L. Rogozinski. 1986. Human helper-T-cell function does not require T4 antigen expression. *Cell Immunol.* 103:105.
52. Poo, W. J., L. Conrad, and C. A. Janeway. 1988. Receptor-directed focusing of lymphokine release by helper T cells. *Nature* 332:378.
53. Sekita, K., C. Straub, D. Hoessli, and R. H. Zubler. 1988. B cell-stimulating activity of lymphoid cell membrane fractions. *Eur. J. Immunol.* 18:1405.
54. Hodgkin, P. D., L. C. Yamashita, R. L. Coffman, and M. R. Kehry. 1990. Separation of events mediating B cell proliferation and Ig production by using T cell membranes and lymphokines. *J. Immunol.* 145:2025.
55. Noelle, R. J., J. Daum, W. C. Bartlett, J. McCann, and D. M. Shepherd. 1991. Cognate interactions between helper T cells and B cells. V. Reconstitution of T helper cell function using purified plasma membranes from activated Th1 and Th2 helper cells and lymphokines. *J. Immunol.* 146:1118.
56. Kubota, E., D. T. McKenzie, R. W. Dutton, and S. L. Swain. 1991. Role of T cells in the B-cell response: glutaraldehyde-fixed T-helper hybridoma cells synergize with the lymphokines IL-4 to induce B-cell activation and proliferation. *Immunology.* 72:40.
57. Crow, M. K., B. Kushner, J. A. Jovers, S. M. Friedman, S. E. Mechanic, and W. Stohl. 1989. Human peripheral blood T helper cell-induced B cell activation results in B cell surface expression of the CD23 (BLAST-2) antigen. *Cell Immunol.* 121:99.
58. Shields, J. G., R. J. Armitage, B. N. Jamieson, P. C. Beverley, and R. E. Callard. 1989. increased expression of surface IgM but not IgD or IgG on human B cells in response to IL-4. Immunology 66:224.
59. Kirchevsky, A., E. G. Armstrong, J. Schlatterer, S. Birken, J. O'Connor, K. Bikel, S. Silverberg, J. W. Lustbader, and R. E. Canfield. 1988. Preparation and characterization of antibodies to the urinary fragment of the human chorionic gonadotropin beta-subunit. *Endocrinology* 123:584.
60. Bank, I., R. A. DePinho, M. B. Brenner, J. Cassimeris, F. W. Alt, and L. Chess. 1986. A functional T3 molecule associated with a novel heterodimer on the surface of immature human thymocytes. *Nature* 322:179.
61. Crow, M. K. and H. G. Kunkel. 1985. Activated B lymphocytes: stimulators of an augmented autologous mixed leukocyte reaction. *Cell Immunol.* 90:555.
62. Friedman, S. M., J. N. Breard, and L. Chess. 1976. Triggering of human peripheral blood B cells: polyclonal induction and modulation of an in vitro PFC response. *J. Immunol.* 117:2021.
63. Martin, P. J., J. A. Ledbetter, Y. Morishita, C. H. June, P. G. Beatty, and J. A. Hansen. 1986. A 44 kilodalton cell surface homodimer regulates interleukin 2 production by activated human T lymphocytes. *J. Immunol.* 136:3282.
64. Bjorndahl, J. M., S. Nakamura, T. Hara, L. K. Jung, and S. M. Fu. 1988. The 28-kDa/32-kDa activation antigen EA1. Further characterization and signal requirements for its expression. *J. Immunol.* 141:4094.
65. Doech, H. M., R. K. Schuurrnan, and E. W. Gelfant. 1980. Polyclonal activation of human lymphocytes in vitro-II. Reappraisal of T and B cell-specific mitogens. *J. Immunol.* 125:827.
66. Rabin, E. M., J. Ohara, and W. E. Paul. 1985. B-cell stimulatory factor 1 activates resting B cells. Proc. Natl. Acad. Sci. U.S. A. 82:2935.

What is claimed is:

1. A protein free of cell membranes and other cellular components, wherein said protein is capable of being expressed by activated T cells and/or the Jurkat D1.1 cell line having ATCC Accession No. CRL 10915 and is specifically recognized by an antibody that specifically binds an epitope that is specifically bound by monoclonal antibody 5c8 produced by the hybridoma having ATCC Accession No. HB 10916.

2. A protein that is a fragment of a protein specifically recognized by monoclonal antibody 5c8 produced by the hybridoma having ATCC Accession No. HB 10916, wherein said protein specifically recognized by monoclonal antibody 5c8 is capable of being expressed by activated T cells and/or the Jurkat D1.1 cell line having ATCC Accession No. CRL 10915 and wherein said fragment is free of cell membranes and other cellular components, comprises an epitope that is specifically bound by monoclonal antibody 5c8 produced by the hybridoma having ATCC Accession No. HB 10916, and is capable of inducing activation of B cells.

3. A protein free of cell membranes and other cellular components, said protein consisting essentially of an epitope that is specifically bound by monoclonal antibody 5c8 produced by the hybridoma having ATCC Accession No. HB 10916 and being capable of inducing activation of B cells.

4. A labeled protein comprising a protein according to any one of claims 1, 2 and 3, wherein said protein is labeled with a detectable marker.

5. The labeled protein according to claim 4, wherein the detectable marker is a radioactive isotope, enzyme, dye or biotin.

6. A composition comprising the protein according to any one of claims 1, 2 and 3 and a carrier.

* * * * *